(12) United States Patent
Müller et al.

(10) Patent No.: US 6,670,347 B2
(45) Date of Patent: Dec. 30, 2003

(54) 19-NOR-17α-PREGNA-1,3,5(10)-TRIEN-17β-OLS WITH A 21,16α-LACTONE RING

(75) Inventors: Gerd Müller, Jena (DE); Uwe Kollenkirchen, Berlin (DE); Dirk Kosemund, Erfurt (DE); Karl-Heinrich Fritzemeier, Berlin (DE); Walter Elger, Berlin (DE)

(73) Assignee: Schering AG, Berlin (DE)

( * ) Notice: Subject to any disclaimer, the term of this patent is extended or adjusted under 35 U.S.C. 154(b) by 0 days.

(21) Appl. No.: 09/963,685

(22) Filed: Sep. 27, 2001

(65) Prior Publication Data

US 2002/0156271 A1 Oct. 24, 2002

Related U.S. Application Data

(60) Provisional application No. 60/243,285, filed on Oct. 26, 2000.

(30) Foreign Application Priority Data

Sep. 27, 2000 (DE) .......................... 100 48 634

(51) Int. Cl.⁷ ............... A61K 31/585; A61K 31/58; C07J 1/00; C07J 7/00; C07J 71/00
(52) U.S. Cl. ............ 514/175; 514/182; 514/825; 540/72; 552/558; 552/617
(58) Field of Search ................... 514/175, 182, 514/825; 540/72; 552/617, 558

(56) References Cited

U.S. PATENT DOCUMENTS 5,698,545 A  * 12/1997 Clark et al. ............. 514/179

OTHER PUBLICATIONS

Hobe et al., Steroids, vol. 36(2), pp. 131–147, 1980.*

* cited by examiner

*Primary Examiner*—Barbara P. Badio
(74) *Attorney, Agent, or Firm*—Millen, White, Zelano & Branigan, P.C.

(57) ABSTRACT

This invention relates to new 19-nor-17α-pregna-1,3,5(10)-trien-17β-ols with a 21,16α-lactone ring of formula II,

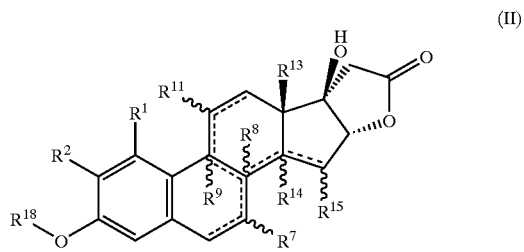

process for their production and pharmaceutical preparations that contain these compounds as well as 17α-cyanomethylated estra-1,3,5(10)-trienes, which produce intermediate products on the way to the 19-nor-17α-pregna-1,3,5(10)-trien-17β-ols.

The 19-nor-17α-pregna-1,3,5(10)-trien-17β-ols produce novel selective estrogens, which contrast to standard estrogens, such as estradiol, show a preference for one of the two known estrogen receptors, estrogen receptor alpha.

32 Claims, No Drawings

19-NOR-17α-PREGNA-1,3,5(10)-TRIEN-17β-OLS WITH A 21,16α-LACTONE RING

This application claims the benefit of the filing date of U.S. Provisional Application Serial No. 60/243,285 filed Oct. 26, 2000.

This invention relates to new 19-nor-17α-pregna-1,3,5 (10)-trien-17β-ols with a 21,16α-lactone ring, process for their production and pharmaceutical preparations that contain these compounds, as well as 17α-cyanomethylated estra-1,3,5(10)-trienes, which produce intermediate products on the way to the 19-nor-17α-pregna-1,3,5(10)-trien-17β-ols.

The 19-nor-17α-pregna-1,3,5(10)-trien-17β-ols with a 21,16α-lactone ring produce novel selective estrogens that in contrast to standard estrogens, such as estradiol, show a preference for one of the two known estrogen receptors, estrogen receptor alpha (ERα; Kuiper et al. (1996), Proc. Natl. Acad. Sci. 93:5925–5930; Mosselman, Dijkema (1996) Febs Letters 392:49–53 (and EP-A-0 798 378); Tremblay et al. (1997), Molecular Endocrinology 11:353–365). Since the two estrogen receptors, ERα and ERβ, have a different organ distribution (Kuiper et al. (1996), Endocrinology 138:863–870), the ERα tracing of selective estrogens represents an important technical step forward. With these new estrogens, a more selective therapy of estrogen-deficiency-induced diseases with low estrogen action on organs that do not express ERα is possible.

Estrogens exert their physiological action on a receptor protein, estrogen receptor (ER). In this case, this is a nuclear-position transcription factor that can be activated by ligands. Until a few years ago, it was assumed that estrogens exert their action on a single receptor. Recently, ERβ was discovered as a second subtype of the estrogen receptor (Kuiper et al. (1996), Proc. Natl. Acad. Sci. 93:5925–5930; Mosselman, Dijkema (1996) Febs Letters 392:49–53; Tremblay et al. (1997), Molecular Endocrinology 11:353–365). The expression pattern of ERG was distinguished from that of the ERA (Kuiper et al. (1996), Endocrinology 138:863–870). Thus, relative to ERα, ERβ predominates in the rat prostates, while ERα predominates in the rat uterus. In the brain, areas were identified in which in each case only one of the two ER-subtypes is expressed (Shugrue et al. (1996), Steroids 61:678–681), Li et al. (1997), Neuroendocrinology 66:63–67). In bones (Kuiper et al. (1998), Frontiers in Neuroendocrinology 19:253–286) and blood vessels, both ERα and ERβ are expressed (Iafrati et al. (1997) Nature Med. 3:545–48).

Because of the different tissue distribution, it was possible to achieve a selective estrogen action by subtype-specifice ligands. Substances with preference for ERβ compared to ERα in the in-vitro receptor binding test were described by Kuiper et al. (Kuiper et al. (1996), Endocrinology 138:863–870). In addition, ERβ-selective estrogens were described in separate patent applications (DE 199 06 159, DE 199 17 930 and DE 199 54 105), as well as in a patent application of Sumitomo Chemicals Co. [JP 11292872; JP 1998-90296]. Patents by Katzenellenbogen et al. (WO 00/19994; PCT/US99/22747) and Loozen et al. (PCT/EP99/09053; WO 00/31112) describe subtype-specific estrogen receptor ligands, i.a., ERα-selective compounds.

This invention is based on the surprising finding that 19-nor-17α-pregna-1,3,5(10)-trienes with a 21,16α-lactone ring have a higher binding affinity to ERα.

This invention consequently relates to 19-nor-17α-pregna-1,3,5(10)-trienes with a 21,16α-lactone ring of general formula (II)

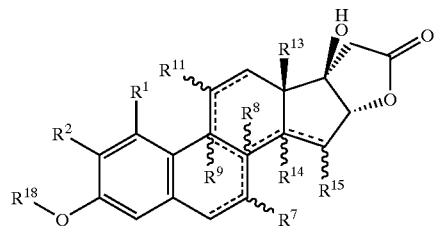

(II)

in which the dotted lines in rings B, C and D optionally mean one or two double bonds, and $R^1$, $R^2$, $R^7$ to $R^9$, $R^{11}$, $R^{13}$ to $R^{15}$ and $R^{18}$, independently of one another, have the following meanings:

$R^1$ means a halogen atom, a hydroxyl, methyl, trifluoromethyl, methoxy or ethoxy group or a hydrogen atom, $R^2$ means a halogen atom, hydroxyl group, straight-chain or branched-chain, saturated or unsaturated alkoxy group with 1 to 6 carbon atoms or a hydrogen atom, $R^7$ means an α- or β-position halogen atom, an α- or β-position, straight-chain or branched-chain, saturated or unsaturated, optionally partially or completely fluorinated alkyl group with up to 10 carbon atoms, straight-chain or branched-chain, saturated or unsaturated alkoxy group with up to 6 carbon atoms, an optionally substituted aryl or heteroaryl radical or a hydrogen atom, $R^8$ means an α- or β-position hydrogen atom, an α- or β-position, straight-chain or branched-chain, saturated or unsaturated, optionally partially or completely fluorinated alkyl group with up to 10 carbon atoms or an α- or β-position cyano group, $R^9$ means an α- or β-position hydrogen atom, an α- or β-position methyl, ethyl, trifluoromethyl or pentafluoroethyl group, $R^{11}$ means an α- or β-position nitrooxy group, an α- or β-position hydroxyl- or mercapto group, an α- or β-position halogen atom, an α- or β-position chloromethyl group, an α- or β-position, straight-chain or branched-chain, saturated or unsaturated, optionally partially or completely fluorinated alkyl group with up to 17 carbon atoms, an α- or β-position, straight-chain or branched-chain, saturated or unsaturated alkoxy or alkylthio group with up to 6 carbon atoms, an optionally substituted, α- or β-position aryl or heteroaryl radical or hydrogen atom, $R^{13}$ means a methyl or ethyl group, $R^{14}$ means an α- or β-position, straight-chain or branched-chain, saturated or unsaturated, optionally partially or completely fluorinated alkyl group with up to 10 carbon atoms or an α- or β-position hydrogen atom, $R^{15}$ means an α- or β-position, straight-chain or branched-chain, saturated or unsaturated, optionally partially or completely fluorinated alkyl group with up to 10 carbon atoms or an α- or β-position hydrogen atom, $R^{14}$ and $R^{15}$ together mean a 14β,15β-methylene group that is optionally substituted with one or two halogen atoms, and $R^{18}$ means a hydrogen atom, methyl, $C_{2-6}$ acyl or tri($C_{1-4}$ alkyl)silyl group or a group $R^{19}SO_2$, whereby $R^{19}$ means a group $R^{20}R^{21}N$, whereby $R^{20}$ and $R^{21}$, independently of one another, represent a hydrogen atom, a $C_{1-5}$ alkyl radical, a group $C(O)R^{22}$, in which $R^{22}$ can contain a straight-chain or branched hydrocarbon radical with up to 12 carbon atoms, which in addition can contain up to three double bonds, a $C_{3-7}$ cycloalkyl radical, an aryl radical or a combination of these structural features, or together with the N-atom means a polymethylenimino radical with 4- to 6 C-atoms or a morpholino radical, whereby the 3,17β-dihydroxy-2-methoxy-19-nor-17α-pregna-1,3,5(10)-triene-21,16α-lactone is excluded.

The substances that are described in this invention produce ERα-selective estrogens, which relative to the above-mentioned compounds are distinguished by a novel structural type and a specific profile of action.

The 3,17β-dihydroxy-2-methoxy-19-nor-17α-pregna-1,3,5(10)-triene-21,16α-lactone excluded per disclaimer was found in metabolite studies of 17α-cyanomethyl-3-methoxy-estra-1,3,5(10)-trien-17β-ol (G. Hobe, R. Schön, W. Schade, Steroids 36 (1980) 131).

According to the invention, 19-nor-17α-pregna-1,3,5(10)-trienes with a 21,16α-lactone ring of general formula (IIa)

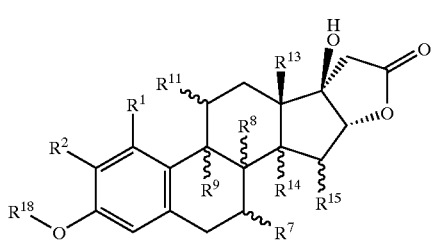

in which $R^1$, $R^2$, $R^7$ to $R^9$, $R^{11}$, $R^{13}$ to $R^{15}$ and $R^{18}$ have the above-indicated meaning, whereby among the latter, 19-nor-17α-pregna-1,3,5(10)-trienes are preferred, in which $R^1$, $R^2$, $R^7$, $R^8$, $R^{11}$ and $R^{13}$ to $R^{15}$ mean a hydrogen atom, $R^9$ means a $C_{1-4}$ alkyl group and $R^{18}$ means a hydrogen atom or a methyl group, in which $R^1$, $R^2$, $R^7$, $R^8$, $R^9$ and $R^{13}$ to $R^{15}$ mean a hydrogen atom, $R^{11}$ means a $C_{1-6}$ alkyl group, $C_{1-6}$ alkoxy group, vinyl group or phenyl group, and $R^{18}$ means a hydrogen atom or a methyl group, or in which $R^1$, $R^2$, $R^8$, $R^9$, $R^{11}$ and $R^{13}$ to $R^{15}$ mean a hydrogen atom, $R^7$ means a $C_{1-4}$ alkyl group, $C_{1-4}$ alkoxy group, vinyl group or phenyl group, and $R^{18}$ means a hydrogen atom or a methyl group, are preferred.

Examples of preferred 19-nor-17α-pregna-1,3,5(10)-trienes with a 21,16α-lactone ring are:

1. 3,17β-Dihydroxy-11β-methyl-19-nor-17α-pregna-1,3,5(10)-triene-21,16α-lactone,
2. 3,17β-Dihydroxy-3-methoxy-11β-methyl-19-nor-17α-pregna-1,3,5(10)-triene-21,16α-lactone,
3. 3,17β-Dihydroxy-11β-methoxy-19-nor-17α-pregna-1,3,5(10)-triene-21,16α-lactone,
4. 3,17α-Dihydroxy-3,11β-dimethoxy-19-nor-17α-pregna-1,3,5(10)-triene-21,16α-lactone,
5. 3,17β-Dihydroxy-11β-ethyl-19-nor-17α-pregna-1,3,5(10)-triene-21,16α-lactone,
6. 3,17β-Dihydroxy-11β-ethyl-3-methoxy-19-nor-17α-pregna-1,3,5(10)-triene-21,16α-lactone,
7. 3,17β-Dihydroxy-11β-phenyl-19-nor-17α-pregna-1,3,5(10)-triene-21,16α-lactone,
8. 3,17β-Dihydroxy-3-methoxy-11β-phenyl-19-nor-17α-pregna-1,3,5(10)-triene-21,16α-lactone,
9. 3,17β-Dihydroxy-11β-vinyl-19-nor-17α-pregna-1,3,5(10)-triene-21,16α-lactone,
10. 3,17β-Dihydroxy-3-methoxy-11β-vinyl-19-nor-17α-pregna-1,3,5(10)-triene-21,16α-lactone,
11. 3,17β-Dihydroxy-7β-methyl-19-nor-17α-pregna-1,3,5(10)-triene-21,16α-lactone,
12. 3,17β-Dihydroxy-3-methoxy-7β-methyl-19-nor-17α-pregna-1,3,5(10)-triene-21,16α-lactone,
13. 3,17β-Dihydroxy-7β-methoxy-19-nor-17α-pregna-1,3,5(10)-triene-21,16α-lactone,
14. 3,17β-Dihydroxy-3,7β-dimethoxy-19-nor-17α-pregna-1,3,5(10)-triene-21,16α-lactone,
15. 3,17β-Dihydroxy-7β-ethyl-19-nor-17α-pregna-1,3,5(10)-triene-21,16α-lactone,
16. 3,17β-Dihydroxy-7β-ethyl-3-methoxy-19-nor-17α-pregna-1,3,5(10)-triene-21,16α-lactone,
17. 3,17β-Dihydroxy-7β-phenyl-19-nor-17α-pregna-1,3,5(10)-triene-21,16α-lactone,
18. 3,17β-Dihydroxy-3-methoxy-7β-phenyl-19-nor-17α-pregna-1,3,5(10)-triene-21,16α-lactone,
19. 3,17β-Dihydroxy-7β-vinyl-19-nor-17α-pregna-1,3,5(10)-triene-21,16α-lactone,
20. 3,17β-Dihydroxy-3-methoxy-7β-vinyl-19-nor-17α-pregna-1,3,5(10)-triene-21,16α-lactone,
21. 3,17β-Dihydroxy-7α-methyl-19-nor-17α-pregna-1,3,5(10)-triene-21,16α-lactone,
22. 3,17β-Dihydroxy-3-methoxy-7α-methyl-19-nor-17α-pregna-1,3,5(10)-triene-21,16α-lactone,
23. 3,17β-Dihydroxy-7α-methoxy-19-nor-17α-pregna-1,3,5(10)-triene-21,16α-lactone,
24. 3,17β-Dihydroxy-3,7α-dimethoxy-19-nor-17α-pregna-1,3,5(10)-triene-21,16α-lactone,
25. 3,17β-Dihydroxy-7α-ethyl-19-nor-17α-pregna-1,3,5(10)-triene-21,16α-lactone,
26. 3,17β-Dihydroxy-7α-ethyl-3-methoxy-19-nor-17α-pregna-1,3,5(10)-triene-21,16α-lactone,
27. 3,17β-Dihydroxy-7α-phenyl-19-nor-17α-pregna-1,3,5(10)-triene-21,16α-lactone,
28. 3,17β-Dihydroxy-3-methoxy-7α-phenyl-19-nor-17α-pregna-1,3,5(10)-triene-21,16α-lactone,
29. 3,17β-Dihydroxy-7α-vinyl-19-nor-17α-pregna-1,3,5(10)-triene-21,16α-lactone,
30. 3,17β-Dihydroxy-3-methoxy-7α-vinyl-19-nor-17α-pregna-1,3,5(10)-triene-21,16α-lactone,
31. 3,17β-Dihydroxy-19-nor-17α-pregna-1,3,5(10)-triene-21,16α-lactone or
32. 3,17β-Dihydroxy-3-methoxy-19-nor-17α-pregna-1,3,5(10)-triene-21,16α-lactone.

In addition, 19-nor-17α-pregna-1,3,5(10)-trienes with a 21,16α-lactone ring of general formula (IIb)

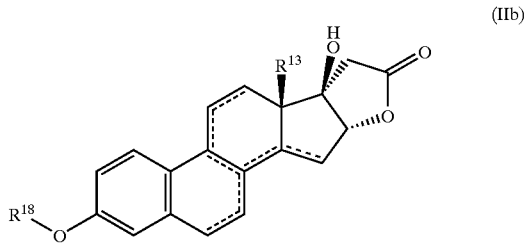

are preferred, in which the dotted lines in rings B, C and D optionally mean one or two double bonds, and $R^{13}$ and $R^{18}$ have the above-indicated meaning, whereby among these compounds, 19-nor-17α-pregna-1,3,5(10)-trienes with a 21,16α-lactone ring are preferred, which have additional double bonds in 7,8-position, 6,7-position, 8,9-position, 9,11-position or 6,7-position and 8,9-position, or in which $R^{18}$ means a hydrogen atom or a methyl group.

In this connection, examples of preferred 19-nor-17α-pregna-1,3,5(10)-trienes with a 21,16α-lactone ring and additional double bonds are:
1. 3,17β-Dihydroxy-19-nor-17α-pregna-1,3,5(10),7-tetraene-21,16α-lactone,
2. 3,17β-Dihydroxy-3-methoxy-19-nor-17α-pregna-1,3,5(10),7-tetraene-21,16α-lactone,
3. 3,17β-Dihydroxy-19-nor-17α-pregna-1,3,5,6,8(9)-pentaene-21,16α-lactone,
4. 3,17β-Dihydroxy-3-methoxy-19-nor-17α-pregna-1,3,5,6,8(9)-pentaene-21,16α-lactone,
5. 3,17β-Dihydroxy-19-nor-17α-pregna-1,3,5(10),9-tetraene-21,16α-lactone,
6. 3,17β-Dihydroxy-3-methoxy-19-nor-17α-pregna-1,3,5(10),9-tetraene-21,16α-lactone,
7. 3,17β-Dihydroxy-19-nor-17α-pregna-1,3,5(10),8(9)-tetraene-21,16α-lactone or
8. 3,17β-Dihydroxy-3-methoxy-19-nor-17α-pregna-1,3,5(10),8(9)-tetraene-21,16α-lactone.

This invention also relates to 17α- or 17β-cyanomethylated estra-1,3,5(10)-trienes of general formula (I'),

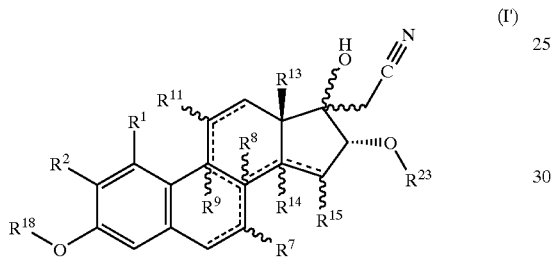

in which the dotted lines in rings B, C, and D optionally mean one or two double bonds, and $R^1$, $R^2$, $R^4$, $R^7$ to $R^9$, $R^{11}$, $R^{13}$ to $R^{15}$, $R^{18}$ and $R^{23}$, independently of one another, have the following meaning:

$R^1$ means a halogen atom; hydroxyl, methyl, trifluoromethyl, methoxy or ethoxy group or a hydrogen atom, $R^2$ means a halogen atom, hydroxyl group, straight-chain or branched-chain, saturated or unsaturated alkoxy group with 2 to 6 carbon atoms or a hydrogen atom, $R^7$ means an α- or β-position halogen atom, an α- or β-position, straight-chain or branched-chain, saturated or unsaturated, optionally partially or completely fluorinated alkyl group with up to 10 carbon atoms, a straight-chain or branched-chain, saturated or unsaturated alkoxy group with up to 6 carbon atoms, an optionally substituted aryl or heteroaryl radical or a hydrogen atom, $R^8$ means an α- or β-position hydrogen atom, an α- or β-position, straight-chain or branched-chain, saturated or unsaturated, optionally partially or completely fluorinated alkyl group with up to 10 carbon atoms or an α- or β-position cyano group, $R^9$ means an α- or β-position hydrogen atom, an α- or β-position methyl, ethyl, trifluoromethyl or pentafluoroethyl group, $R^{11}$ means an α- or β-position nitrooxy group, an α- or β-position hydroxyl or mercapto group, an α- or β-position halogen atom, an α- or β-position chloromethyl group, an α- or β-position, straight-chain or branched-chain, saturated or unsaturated, optionally partially or completely fluorinated alkyl group with up to 10 carbon atoms, an α- or β-position, straight-chain or branched-chain, saturated or unsaturated alkoxy or alkylthio group with up to 6 carbon atoms, an optionally substituted, α- or β-position aryl or heteroaryl radical or hydrogen atom, $R^{13}$ means a methyl or ethyl group, $R^{14}$ means an α- or β-position, straight-chain or branched-chain, saturated or unsaturated, optionally partially or completely fluorinated alkyl group with up to 10 carbon atoms or an α- or β-position hydrogen atoms;

$R^{15}$ means an α- or β-position, straight-chain or branched-chain, saturated or unsaturated, optionally partially or completely fluorinated alkyl group with up to 10 carbon atoms or an α- or β-position hydrogen atom, $R^{14}$ and $R^{15}$ together mean a 14α,15α-methylene or 14β,15β-methylene group optionally substituted with one or two halogen atoms, $R^{18}$ means a hydrogen atom; a methyl-, $C_{2-6}$ acyl or tri($C_{1-4}$ alkyl)silyl group or a group $R^{19}SO_2^-$, whereby $R^{19}$ means a group $R^{20}R^{21}N-$, whereby $R^{20}$ and $R^{21}$, independently of one another, represent a hydrogen atom, a $C_{1-5}$ alkyl radical, a group $C(O)R^{22}$, in which $R^{22}$ can contain a straight-chain or branched hydrocarbon radical with up to 12 carbon atoms, which in addition can contain up to three double bonds, a $C_{3-7}$ cycloalkyl radical, an aryl radical or a combination of these structural features, or together with the N-atom means a polymethylenimino radical with 4 to 6 C atoms or a morpholino radical, and $R^{23}$ means a hydrogen atom, a $C_{2-6}$ acyl or tri($C_{1-4}$ alkyl)silyl group.

The 17α-cyanomethylated estra-1,3,5(10)-trienes of general formula (I)

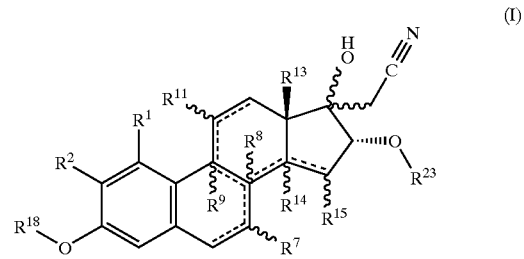

in which $R^1$, $R^2$, $R^7$ to $R^9$, $R^{11}$, $R^{13}$ to $R^{15}$, $R^{18}$ and $R^{23}$ have the above-indicated meaning, are intermediate products on the way to 19-nor-17α-pregna-1,3,5(10)-trienes with a 21,16α-lactone ring of general formula (II). The 17β-cyanomethylated estra-1,3,5(10)-trienes of general formula (I) result in the production of the 19-nor-17α-pregna-1,3,5(10)-trienes of general formula (II).

Preferred according to the invention are 17α-cyanomethylated estra-1,3,5(10)-trienes of general formula (Ia)

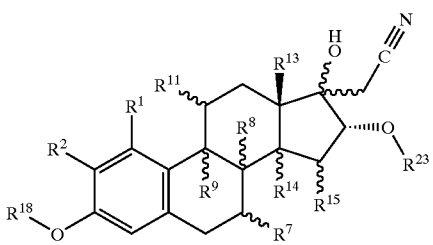

(Ia)

in which $R^1$, $R^2$, $R^7$ to $R^9$, $R^{11}$, $R^{13}$ to $R^{15}$, $R^{18}$ and $R^{23}$ have the above-indicated meaning, whereby among these compounds, in turn those are preferred in which $R^1$, $R^2$, $R^7$, $R^8$, $R^{11}$, $R^{13}$ to $R^{15}$ and $R^{23}$ mean a hydrogen atom, $R^9$ means a $C_{1-4}$ alkyl group and $R^{18}$ means a hydrogen atom or a methyl group, in which $R^1$, $R^2$, $R^7$, $R^8$, $R^{11}$, $R^{13}$ to $R^{15}$ and $R^{23}$ mean a hydrogen atom, $R^{11}$ means a $C_{1-4}$ alkyl group, $C_{1-4}$ alkoxy group, vinyl group or phenyl group, and $R^{18}$ means a hydrogen atom or a methyl group, or in which $R^1$, $R^2$, $R^8$, $R^9$, $R^{11}$, $R^{13}$ to $R^{15}$ and $R^{23}$ mean a hydrogen atom, $R^7$ means a $C_{1-4}$ alkyl group, $C_{1-4}$ alkoxy group, vinyl group or phenyl group, and $R^{18}$ means a hydrogen atom or a methyl group.

Examples of preferred 17α-cyanomethylated estra-1,3,5 (10)-trienes are:
1. 17α-Cyanomethyl-9α-methyl-estra-1,3,5(10)-triene-3,16α,17β-triol,
2. 17α-Cyanomethyl-3-methoxy-9α-methyl-estra-1,3,5 (10)-triene-16α,17β-diol,
3. 17α-Cyanomethyl-estra-1,3,5(10)-triene-3,16α,17β-triol,
4. 17α-Cyanomethyl-3-methoxy-estra-1,3,5(10)-triene-16α,17β-diol,
5. 17α-Cyanomethyl-11β-methyl-estra-1,3,5(10)-triene-3,16α,17β-triol,
6. 17α-Cyanomethyl-11β-methoxy-estra-1,3,5(10)-triene-3,16α,17β-triol,
7. 17α-Cyanomethyl-11β-ethyl-estra-1,3,5(10)-triene-3,16α,17β-triol,
8. 17α-Cyanomethyl-11β-phenyl-estra-1,3,5(10)-triene-3,16α,17β-triol,
9. 17α-Cyanomethyl-11β-vinyl-estra-1,3,5(10)-triene-3,16α,17β-triol,
10. 17β-Cyanomethyl-11β-ethyl-estra-1,3,5(10)-triene-3,16α,17α-triol,
11. 17α-Cyanomethyl-7α-methyl-estra-1,3,5(10)-triene-3,16α,17β-triol,
12. 17α-Cyanomethyl-7α-ethyl-estra-1,3,5(10)-triene-3,16α,17β-triol,
13. 17α-Cyanomethyl-7α-phenyl-estra-1,3,5(10)-triene-3,16α,17β-triol,
14. 17α-Cyanomethyl-7α-vinyl-estra-1,3,5(10)-triene-3,16α,17β-triol,
15. 17α-Cyanomethyl-3-methoxy-11β-methyl-estra-1,3,5 (10)-triene-16α,17β-diol,
16. 17α-Cyanomethyl-3,11β-dimethoxy-estra-1,3,5(10)-triene-16α,17β-diol,
17. 17α-Cyanomethyl-11β-ethyl-3-methoxy-estra-1,3,5 (10)-triene-16α,17β-diol,
18. 17α-Cyanomethyl-3-methoxy-11β-phenyl-estra-1,3,5 (10)-triene-16α,17β-diol,
19. 17α-Cyanomethyl-3-methoxy-11β-vinyl-estra-1,3,5 (10)-triene-16α,17β-diol,
20. 17α-Cyanomethyl-3-methoxy-6α-methyl-estra-1,3,5 (10)-triene-16α,17β-diol,
21. 17α-Cyanomethyl-7α-ethyl-3-methoxy-estra-1,3,5(10)-triene-16α,17β-diol,
22. 17α-Cyanomethyl-3-methoxy-7α-phenyl-estra-1,3,5 (10)-triene-16α,17β-diol or
23. 17α-Cyanomethyl-3-methoxy-7α-vinyl-estra-1,3,5(10)-triene-16α,17β-diol.

In addition, 17α-cyanomethylated estra-1,3,5(10)-trienes of general formula (Ib) according to the invention

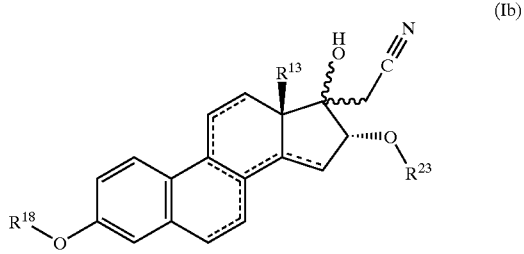

(Ib)

are preferred, in which the dotted lines in rings B, C and D optionally have one or two double bonds, and $R^{13}$, $R^{18}$ and $R^{23}$ have the above-indicated meaning, whereby these compounds can have additional double bonds in 7,8-position, 6,7-position, 8,9-position, 9,11-position or 6,7-position and 8,9-position or $R^{~}$preferably means a hydrogen atom or a methyl group.

In this connection, examples of preferred 17α-cyanomethylated estra-1,3,5(10)-trienes with additional double bonds are:
1. 17α-Cyanomethyl-estra-1,3,5(10),7-tetraene-3,16α,17β-triol,
2. 17α-Cyanomethyl-3-methoxy-estra-1,3,5(10),7-tetraene-16α,17β-diol,
3. 17α-Cyanomethyl-estra-1,3,5,6,8(9)-pentaene-3,16α,17β-triol,
4. 17α-Cyanomethyl-3-methoxy-estra-1,3,5(10),6,8(9)-pentaene-16α,17β-diol,
5. 17α-Cyanomethyl-estra-1,3,5(10),9-tetraene-3,16α,17β-triol,
6. 17α-Cyanomethyl-3-methoxy-estra-1,3,5(10),9-tetraene-16α,17β-diol,
7. 17α-Cyanomethyl-estra-1,3,5(10),8(9)-tetraene-3,16α,17β-triol or
8. 17α-Cyanomethyl-3-methoxy-estra-1,3,5(10),8(9)-tetraene-16α,17β-diol.

In the compounds of general formulas II, IIa and IIb and in the intermediate products of general formulas I, Ia and Ib, a fluorine, chlorine, bromine or iodine atom can always stand for a halogen atom; in each case a fluorine atom is preferred.

The alkoxy groups can contain 1 to 6 carbon atoms in each case, whereby methoxy, ethoxy, propoxy, isopropoxy and tert-butyloxy groups are preferred.

As representatives of the alkylthio groups, for example, the methylthio, ethylthio and trifluoromethylthio groups can be mentioned.

In terms of this invention, an aryl radical is a phenyl, 1- or 2-naphthyl radical, and the phenyl radical is preferred.

Unless expressly indicated otherwise, aryl also always includes a heteroaryl radical. Examples of a heteroaryl radical are the 2-, 3- or 4-pyridinyl radical, the 2- or 3-furyl radical, the 2- or 3-thienyl radical, the 2- or 3-pyrrolyl radical, the 2-, 4- or 5-imidazolyl radical, the pyrazinyl radical, the 2-, 4- or 5-pyrimidinyl radical or the 3- or 4-pyridazinyl radical.

As substitutents for an aryl or heteroaryl radical, for example, a methyl, ethyl, trifluoromethyl, pentafluoroethyl, trifluoromethylthio, methoxy, ethoxy, nitro, cyano, halogen (fluorine, chlorine, bromine, iodine), hydroxy, amino, mono ($C_{1-8}$ alkyl) or di($C_{1-8}$ alkyl)amino, whereby both alkyl groups are identical or different, di(aralkyl)amino, whereby both aralkyl groups are identical or different, can be mentioned.

As representatives of straight-chain or branched-chain alkyl groups with 1–17 carbon atoms, for example, methyl, ethyl, propyl, isopropyl, butyl, isobutyl, tert-butyl, pentyl, isopentyl, neopentyl, heptyl, hexyl, and decyl can be mentioned: methyl, ethyl, propyl and isopropyl are preferred.

The alkyl groups can be partially or completely fluorinated or substituted by 1–5 halogen atoms, hydroxy groups or $C_1$–$C_4$ alkoxy groups.

As perfluorinated alkyl groups, for example, trifluoromethyl, pentafluoroethyl and nonafluorobutyl can be mentioned. Representatives of the partially fluorinated alkyl groups are, for example, 2,2,2-trifluoroethyl, 5,5,5,4,4-pentafluoropentyl, 9,9,9,8,8,7,7,6,6-nonafluorohexyl, etc.

Monochloromethylene, monofluoromethylene or difluoromethylene can stand for the halogen-substituted 14,15-methylene group.

$R^{11}$ in the meaning of an α- or β-position, straighten chain or branched-chain, saturated or unsaturated, optionally partially or completely fluorinated alkyl group can be selected from the following groups according to the invention:

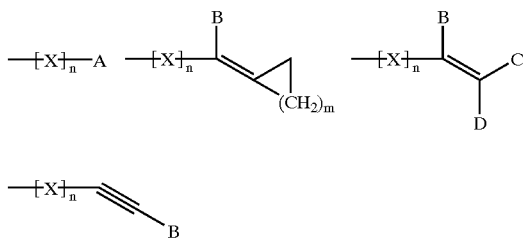

whereby X is $CH_2$, CH—$C_{1-8}$ alkyl or C($C_{1-8}$ alkyl)$_2$, A is a hydrogen atom, a $C_{1-8}$ alkyl group, a $C_3$–$C_7$ cycloalkyl group or together with X forms a $C_3$–$C_7$ ring system; B is a hydrogen atom, a $C_{18}$ alkyl group, a $C_3$–$C_7$ cycloalkyl group; C and D, independently of one another, are a hydrogen atom, a $C_{1-8}$ alkyl group, a $C_3$–$C_7$ cycloalkyl group, optionally substituted with a halogen atom or a cyano-group; n means an integer from 1 to 9 and m means an integer from 1 to 5, whereby $R^{11}$ preferably occupies the β-position. The above-mentioned $C_{1-8}$ alkyl group means a straight-chain or branched alkyl group, such as, for example, methyl, ethyl, propyl, isopropyl, butyl, isobutyl, tert-butyl, pentyl, isopentyl, neopentyl, heptyl, hexyl and octyl. The above-mentioned $C_3$–$C_7$ cycloalkyl group means a monocyclic group or bicyclic group, such as, for example, cyclopropyl, cyclobutyl, cyclopentyl, or cyclohexyl.

Other variants of the invention provide one or more conjugated double bonds in rings B, C and D of the estratriene skeleton:

A double bond between C atoms 6 and 7 or between C atoms 7 and 8 or between C atoms 8 and 9 or between C atoms 9 and 11 or between C atoms 8 and 14 or between C atoms 14 and 15 or double bonds between C atoms 6 and 7 and C atoms 8 and 9 or between C atoms 8 and 9 and C atoms 14 and 15 or between C atoms 6 and 7, C atoms 8 and 9 and C atoms 11 and 12 or between C atoms 6 and 7, C atoms 8 and 9 and C atoms 14 and 15 or between C atoms 6 and 7, C atoms 8 and 9, C atoms 11 and 12 as well as C atoms 14 and 15.

The hydroxyl group at C atom 3 can be esterified with an aliphatic, straight-chain or branched-chain, saturated or unsaturated $C_{2-6}$ carboxylic acid. As such carboxylic acids for the esterification, for example, acetic acid, propionic acid, butyric acid, isobutyric acid, valeric acid, isovaleric acid or pivalic acid are suitable.

As examples of a tri($C_{1-4}$ alkyl) group, a trimethylsily group and a tert-butyl-direthyl group can be mentioned.

Production of the Compounds According to the Invention

The 17α- and 17β-cyanomethylated estra-1,3,5(10)-trienes of general formula (I') can be obtained by a compound of general formula (III)

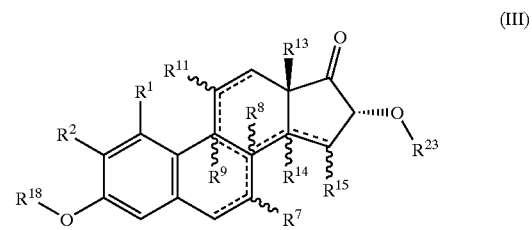

in which the dotted lines in rings B, C and D optionally mean one or two double bonds, $R^1$, $R^2$, $R^4$, $R^7$ to $R^9$, $R^{11}$, $R^{13}$ to $R^{15}$ and $R^{18}$ have the above-indicated meaning, and $R^{23}$ means a hydrogen atom, a butyryl group or a tert-butyldimethyl group, being reacted with lithium acetonitrile.

The 19-nor-17α-pregna-1,3,5(10)-trienes with a 21,16α-lactone ring of general formula (II) can be produced by a compound of general formula (III),

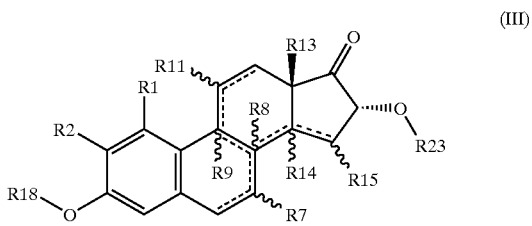

in which the dotted lines in rings B, C and D optionally mean one or two double bonds; $R^1$, $R^2$, $R^4$, $R^7$ to $R^9$, $R^{11}$, $R^{13}$ to $R^{15}$ and $R^{18}$ have the above-indicated meaning, and $R^{23}$ means an acetyl or trimethylsilyl group, being reacted with lithium acetonitrile.

The production of 19-nor-17α-pregna-1,3,5(10)-trienes with a 21,16α-lactone ring can be carried out in a one-stage process from the corresponding 17-oxo compounds or from the 17α-cyanomethylated estra-1,3,5(10)-trienes.

For the lactone formation, substituents $R^{14}$, $R^{15}$ and $R^{23}$ are especially important.

The formation of the iminoether and thus also the lactone is bonded to the presence of a 17α-cyanomethyl substituent.

This is influenced by the substitution in 14- and 15-positions. If hydrogen atoms or β-substituents are found in these positions or the molecules contain a 14,15-double bond, mainly 17α-cyanomethylated estra-1,3,5(10)-trienes, which can be further reacted into lactone, are produced.

If the compound, which is to be reacted with lithium acetonitrile, contains a free hydroxyl group in 16-position, the attack of the lithium acetonitrile on the 17-keto group takes place almost exclusively on the β-side, and thus a lactone formation is no longer possible.

In the case of basic, easily cleavable acyloxy or silyloxy compounds in 16-position, e.g., if $R^{23}$ is an acetyl or trimethylsilyl group, predominantly the corresponding lactone is formed from the 17α-cyanomethylated compounds that are formed as intermediate products. The process for the production of 21,16α-lactones according to the invention is therefore advantageously performed as follows. The compounds of general formula (III), which are substituted with $R^{23}$ trimethylsilyl and acetyl groups, are reacted in a single-pot process with lithium acetonitrile. In this connection, about 60% of 17α-cyanomethylated intermediate product is reacted in situ to 21,16α-lactone.

An iminoether formation and thus lactone formation is almost completely suppressed if base-stable substituents, e.g., tert-butyldimethylsilyloxy or longer-chain acyloxy groups, are present in 16-position. That is, if the cyanomethylation is carried out with compounds of general formula (III), which are substituted with $R^{23}$ tert-butyldimethylsilyl groups, 17α- and 17β-cyanomethylated estra-1,3,5-(10)-trienes of general formula (I') can be isolated in addition to small amounts of 21,16α-lactone. In addition, the size of the 16-substituent promotes the β-addition of the lithium acetonitrile to the 17-oxo group.

In the following reaction diagram ($R^{23}$ is a trimethylsilyl group or acyl group), the corresponding steps are depicted:

rated or unsaturated in rings B, C, and D, with a protected or unprotected 16α-hydroxy group.

These compounds can be produced according to generally known processes.

Characteristic but not limiting synthesis processes, which are useful for providing representative substitution patterns in the estrone skeleton also in combination with several substituents, are found in, for example: C(1) J. Chem. Soc. (C) 1968, 2915; C(7) Steroids 54, 1989, 71 C(8α) Tetrahedron Letters 1991, 743; C(8β) Tetrahedron Letters 1964, 1763; Tetrahedron 1969, 25, 4011; J. Org. Chem. 1970, 35, 468; C(11) J. Steroid Biochem. 31, 1988, 549; Tetrahedron 33, 1977, 609 and J. Org. Chem. 60, 1995, 5316, C(9) DE-A-2035879; J. Chem. Soc. Perk. 1, 1973, 2095; C(15) J. Chem. Soc. Perk. 1, 1996, 1269) and C(14β) Z. Chem. 23, 1983, 410. Etherification and/or esterification of free hydroxy groups is carried out according to the standard methods that are known to one skilled in the art.

The introduction of the 16-hydroxy group is carried out in the conventional way by alkaline hydrolysis of the 16α-bromine compounds or by reaction of silyl- or acylenol ethers with peracids and subsequent hydrolysis.

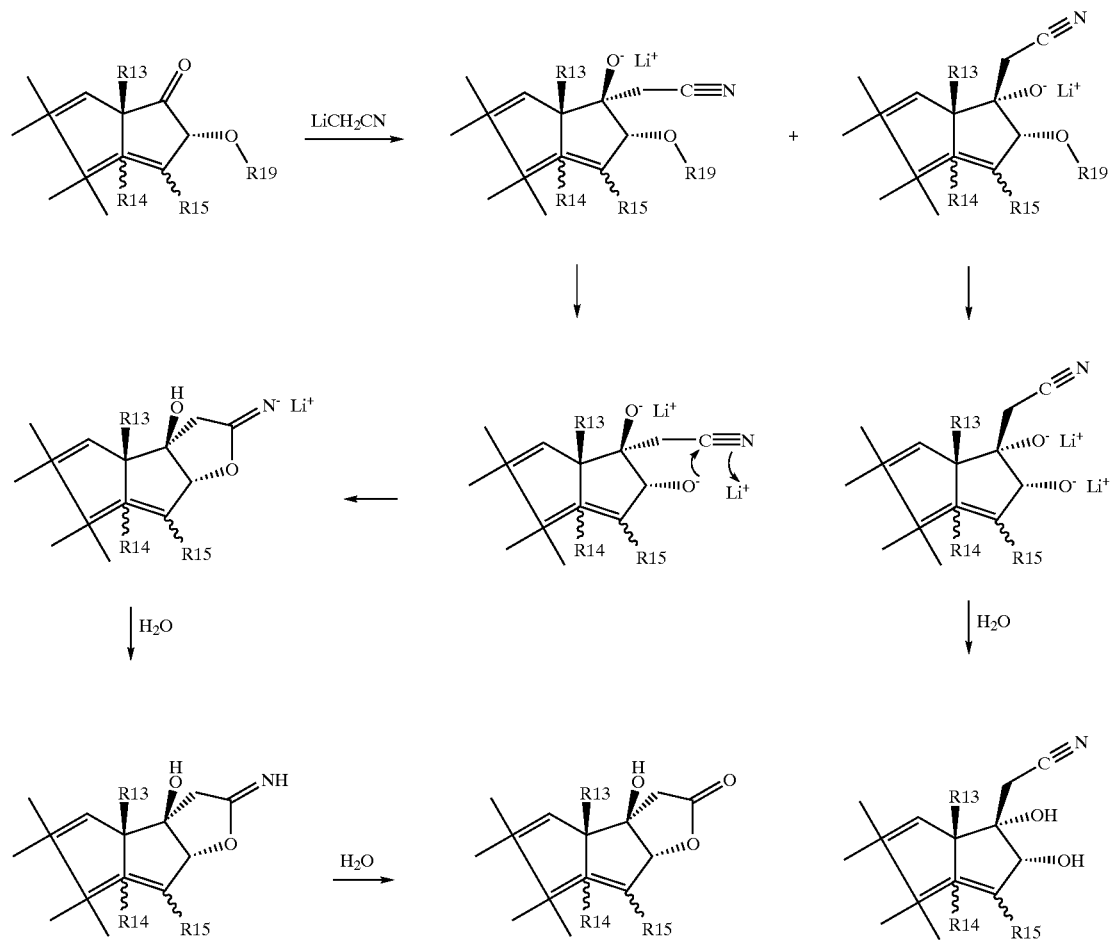

The production of the compounds according to the invention, i.e., the 17α- or 17β-cyanomethylated estra-1,3,5(10)-trienes and the 19-nor-17α-pregna-1,3,5(10)-trienes with 21,16α-lactone rings is based on the reaction of substituted 17-keto steroids or 17-keto steroids that are satu- Pharmaceutical Preparations and Indications This invention comprises the novel lactones as pharmaceutical active ingredients, their production, their therapeutic use, and the pharmaceutical forms for dispensing, which contain the new substances. The chemical compounds are new steroidal selective estrogens.

The novel selective estrogens that are described in this patent can be used as individual components in pharmaceutical preparations or in combination especially with gestagens, androgens or antiestrogens. Like other estrogens, the novel selective estrogens are suitable for treatment of estrogen-deficiency-induced diseases and for contraception. Because of the metabolic stability of the new selective estrogens, they are especially well suited for oral forms of administration.

The substances and the pharmaceutical agents that they contain are suitable as, e.g., components of oral contraceptive agents, for example in combination with a gestagen. They can also be used for the treatment of perimenopausal and postmenopausal symptoms, especially hot flashes, sleep disturbances, irritability, mood swings, incontinence, vaginal atrophy and hormone-deficiency-induced mental disorders in perimenopausal or postmenopausal women. The substances are also suitable for hormone substitution and therapy of hormone-deficiency-induced symptoms in the case of surgical, medicinal or ovarian dysfunction that is caused in some other way.

In addition, the substances for the therapy of osteoporosis in men and women, also in combination With androgens, are suitable.

In addition, the substances can be used for prophylaxis of hormone-deficiency-induced bone mass loss and osteoporosis, for prevention of cardiovascular system diseases, especially vascular diseases, such as arteriosclerosis, and for prevention of hormone-deficiency-induced neurodegenerative diseases, such as Alzheimer's disease, and hormone-deficiency-induced impairment of memory and learning-capacity in women and men.

In addition, the substances can be used for treatment of inflammatory diseases of the immune system, especially auto-immune diseases, such as, e.g., rheumatoid arthritis.

Another field of use is the use of substances for promoting wound healing, as- well as for prevention of age- and hormone-deficiency-induced skin changes.

The therapy of prostate cancer represents another field of use.

Estrogens as Components of Oral Contraceptives

Contraceptive methods that are based on the ovulation inhibition by administration with a combination that consists of an estrogen and a gestagen are very well established. The novel estrogens, which are components of this invention, are especially well suited as estrogenic components of combination preparations for contraception. Target organs of the estrogen in combination preparations are especially the pituitary gland, the ovary and the endometrium. These organs express ERα (Kuiper et al. (1996), Endocrinology 138:863–870). The novel ERα selective estrogens act with greater selectivity on these target organs than previously known estrogens such as estradiol and ethinylestradiol.

Treatment of Hormone-Deficiency-Induced Symptoms and Protective Action of Estrogen on Bones, Brains and Vascular Systems The efficiency of estrogens in the treatment of hormone-deficiency-induced symptoms, such as hot flashes and atrophy of estrogen target organs, and for prevention of bone mass loss in perimenopausal and postmenopausal women is well documented and generally accepted. It is also well documented that estrogen replacement therapy (ERT) in postmenopausal women or in women with ovarian dysfunction that is caused in some other way reduces the risk of cardiovascular diseases relative to non-estrogen-treated women (Grady et al. 1992, Ann. Intern. Med. 117:1016–1037).

Newer studies confirm, moreover, a protective action of estrogens against neurodegenerative diseases, such as, e.g., Alzheimer's disease (Henderson 1997, Neurology 48 (Suppl. 7):27–35; Birge 1997, Neurology 48 (Suppl. 7):36–41), a protective action with respect to brain functions, such as memory and learning capacity (McEwen et al. 1997, Neurology 48 (Suppl. 7):8–15; Sherwin 1997, Neurology 48 (Suppl. 7):21–26), as weld as against hormone-deficiency-induced mood swings (Halbreich 1997, Neurology 48 (Suppl. 7):16–20).

In the conventional estrogen or hormone replacement therapy, standard estrogens, such as estradiol and conjugated estrogens from equine urine, are used either by themselves or in combination with a gestagen, antigestagen or mesoprogestin.

As estrogen components of estrogen/gestagen combination preparations the selective estrogens that are described in this invention are especially well suited: new studies of ERα-knockout mice have shown that ERα can be considered as an essential mediator of the estrogen action in bone, in the vascular system and in the brain. With the novel ERα-selective estrogens, a more specific action with respect to these target organs of the ERT is achieved.

Biological Characterization of the Novel Estrogens According to the Invention

This patent application describes novel structures for selective estrogens, which have in vitro dissociation with respect to binding to estrogen receptor preparations of the rat uterus and rat prostate. In this case, it is assumed that ERα predominates in the rat uteri over ERβ, while ERβ predominates in the rat prostates over ERα. In accordance with this, it was found that the ratio of the binding to the uterus and prostate receptor qualitatively corresponds to the quotient of the relative binding affinity (RBA) to human ERα and ERβ of rats (according to Kuiper et al. (1996), Endocrinology 138:863–870) (cf. DE 199 06 159, DE 199 17 930 and DE 199 54 105).

In the test on protection against estrogen-deficiency-induced bone mass loss in the female rats that have undergone ovariectomy (ovx), the substances have a high estrogenic activity. In addition, they efficiently inhibit the FSH secretion and stimulate the uterus growth in the ovx rat.

Methodology

Estrogen Receptor Binding Studies

The binding affinity of the new selective estrogens was tested in competitive tests with use of 3H-estradiol as a ligand in estrogen receptor preparations of rat prostates and rat uteri. The preparation of the prostate cytosol and the estrogen receptor test was performed with the prostate cytosol, as described by Testas et al. (1981) (Testsas, J. et al., 1981, Endocrinology 109:1287–1289).

The preparation of rat uterus cytosol, and the receptor test with the ER containing cytosol were performed basically as by Stack and Gorski, 1985 (Stack, Gorski 1985, Endocrinology 117, 2024–2032) with some modifications as described in Fuhrmann et al. (1995) (Fuhrmann U. et al. 1995, Contraception 51:45–52).

In Vivo Studies for Determining the Bone-Protective Action of the Compounds According to the Invention The bone-protective action was determined on the female ovx rat. Rats were ovariectomized and treated immediately after the operation with various dosages of test substances or reference substances. The administration of the substances was carried out subcutaneously daily over 20 days. An in-depth description of the method was published elsewhere (K. H. Fritzemeier, Ch. Hegele-Hartung (1999), Handbook of Pharmacol., Oettel, Schillinger Eds. 135/II, 21:1–94).

Uterus Growth Test on Ovariectomized Rats

An in-depth description of the experiment was published (K. H., Fritzemeir, Ch. Hegele-Hartung (1999), Handbook of Pharmacol., Oettel, Schillinger eds., 135/II, 21:1–94). Ovariectomized rats were treated 10 days after ovariectomy with various dosages of the test substance or reference substance. The treatment was carried out subcutaneously daily over 3 days. On day 4, the animals were sacrificed, and the uterus moist and dry weights were determined.

Inhibition of FSH-Secretion and Stimulation of Uterus Growth after a 7-Day Treatment of Ovariectomized Rats Ovariectomized rats were treated 10 days after ovariectomy with various dosages of test substances. The treatment was carried out subcutaneously using osmotic pumps. On day 8 after the beginning of the treatment, the animals were sacrificed, uterus moist and fresh weights were determined, and the FSH level was determined in the serum.

Results

| | Receptor Binding | |
|---|---|---|
| Substance | Rat Uterus Cytosol (RBA*) | Rat Prostate Cytosol (RBA*) |
| 3,17β-Dihydroxy-19-nor-17α-pregna-1,3,5(10)-triene-21, 16α-lactone | 12.5 | <0.1 |

RBA*: Relative binding affinity, RBA of reference substance estradiol = 100

| Uterus Growth Test on Ovariectomized Rats | | |
|---|---|---|
| Substance | Dosage [µg/kg] | Uterus Moist Weight [Mw ± SD] |
| 3,17β-Dihydroxy-19-nor-17α-pregna-1,3,5(10)-triene-21,16α-lactone | 0.1 | 23.7 ± 2.2 |
| | 1 | 60.1 ± 7.4 |
| | 10 | 95.9 ± 12.4 |
| 17β-Estradiol | 0.1 | 28.0 ± 2.0 |
| | 1 | 71.9 ± 9.6 |
| | 10 | 82.3 ± 11.3 |
| Vehicle monitoring | — | 2.9 ± 1.5 |
| | 12.5 | <0.1 |

Bone-protective Action (20-day Treatment), FSH-Reduction and Uterus Action (7-Day Treatment)

Semi-maximal bone protection (ED50), stimulation of the uterus weight and lowering of the FSH level are produced by a dose of 1 (bone protection) or 4 µg/kg (uterus stimulation; FSH reduction) in subcutaneous administration. The substance thus has comparatively strong activity like the reference estrogen estradiol.

The pharmaceutical compositions or pharmaceutical agents according to the invention contain as active ingredient one or more of the compounds according to the invention, optionally mixed with other pharmacologically or pharmaceutically active substances. The production of the pharmaceutical agents is carried out in a known way, whereby the known and commonly used pharmaceutical adjuvants and other commonly used vehicles and diluents can be used.

As such vehicles and adjuvants, for example, those are suitable that are recommended or indicated in the following bibliographic references as adjuvants for pharmaceutics, cosmetics and related fields: Ullmans Encyklopädie der technischen Chemie [Ullman's Encyclopedia of Technical Chemistry], Volume 4 (1953), pages 1 to 39; Journal of Pharmaceutical Sciences, Volume 52 (1963), page 918 ff., issued by Czetsch-Lindenwald, Hilfsstoffe fur Pharmazie und angrenzende Gebiete [Adjuvants for Pharmaceutics and Related Fields]; Pharm. Ind., Number 2, 1961, page 72 and ff.; Dr. H. P. Fiedler, Lexikon der Hilfsstoffe fur Pharmazie, Kosmetik und angrenzende Gebiete [Dictionary of Adjuvants for Pharmaceutics, Cosmetics and Related Fields], Cantor K G, Aulendorf in Württembert 1971.

The compounds can be administered orally or parenterally, for example intraperitoneally, intramuscularly, subcutaneously or percutaneously. The compounds can also be implanted in the tissue. For oral administration, capsules, pills, tablets, coated tablets, etc., are suitable. In addition to the active ingredient, the dosage units can contain a pharmaceutically compatible vehicle, such as, for example, starch, sugar, sorbitol, gelatin, lubricant, silicic acid, talc, etc. For parenteral administration, the active ingredients can be dissolved or suspended in a physiologically compatible diluent. As diluents, very frequently oils are used with or without the addition of a solubilizer, a surfactant, a suspending agent or emulsifier. Examples of oils that are used are olive oil, peanut oil, cottonseed oil, soybean oil, castor oil and sesame oil. The compounds can also be used in the form of a depot injection or an implant preparation, which can be formulated in such a way that a delayed release of active ingredients is made possible. Implants can contain as inert materials, for example, biodegradable polymers or synthetic silicones, such as, for example, silicone gum. In addition, the active ingredients can be added, for example, to a patch for percutaneous administration.

For the production of intravaginal systems (e.g., vaginal rings) or intrauterine systems (e.g., pessaries, coils, IUDs, Mirena$^{(R)}$) that are laden with active compounds of general formula I for local administration, various polymers, such as, for example, silicone polymers, ethylenevinyl acetate, polyethylene or polypropylene, are suitable.

To achieve a better bio-availability of the active ingredient, the compounds can also be formulated as cyclodextrin clathrates. In this respect, the compounds are reacted with α-, β- or γ-cyclodextrin or derivatives thereof (PCT/EP95/02656).

According to the invention, the compounds of general formula I can also be encapsulated with liposomes.

The following examples are to be used to describe the synthesis of the compounds and the practical reaction of this invention, without limiting the latter.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the foregoing and in the following examples, all temperatures are set forth uncorrected in degrees Celsius and, all parts and percentages are by weight, unless otherwise indicated.

The entire disclosures of all applications, patents and publications, cited, and of corresponding German application No. 10048634.7, filed Sep. 27, 2000, and U.S. Provisional Application Serial No. 60/243,285, filed Oct. 26, 2000, are hereby incorporated by reference.

EXAMPLE 1

8 ml (20 mmol) of n-butyllithium solution (2.5 M in toluene) is cooled in a reaction vessel that was rendered inert while being stirred at −25° C. to −35° C. Then, the solution is diluted by adding 8 ml of tetrahydrofuran while being cooled, and it is reacted with 1.15 ml (22 mmol) of acetonitrile in such a way that a temperature of −25° C. to −35° C. is maintained. A white to yellowish suspension of lithium acetonitrile is produced. A solution of 926 mg (2.5 mmol) of 17-oxo-estra-1,3,5(10)-triene-3,16α-diyldiacetate in 8 ml of tetrahydrofuran is added to this suspension, whereby the reaction temperature is maintained at −25° C. to −35° C. After one hour at a temperature of −25° C. to −35° C., the batch is mixed with water, neutralized with dilute hydrochloric acid, the tetrahydrofuran is distilled off, and a crude product mixture is isolated by extraction with ethyl acetate. By chromatography on silica gel 60 (0.040–0.063 mm) with a mixture of chloroform/n-hexane/methanol (45/45/10) as eluant, the following products can be separated and isolated:
a) 3,17β-Dihydroxy-19-nor-17α-pregna-1,3,5(10)-triene-21,16α-lactone
    484 mg (58% of theory; $^1$H-NMR data and melting points, see Table 1)
b) 17β-Cyanomethyl-estra-1,3,5(10)-triene-3,16α,17α-triol
    230 mg (28% of theory) $^1$H-NMR data (400 MHz, DMSO-d$_6$, TMS): 8.97 (s, 3-OH); 7.03 (d, J=8.6 Hz, H-1); 6.49 (dd, J=8.6/2.7 Hz, H-2) 6.41 (d, J=2.7 Hz, H-4); 5.42 (d, J=5.5 Hz, 16-OH); 4.27 (s, 17-OH); 4.01 (m, H-16); 2.69 (m, H-6); 2.66 and 2.59 (—CH$_2$CN, AB-system JAB=16.8 Hz); 0.73 (s, H-18)

EXAMPLE 2

The reaction of 1.28 g (2.5 mmol) of 3,16α-bis (triethylsilyloxy)estra-1,3,5(10)-trien-17-one is performed according to Example 1. The crude product that is obtained is dissolved in tetrahydrofuran, whereby by adding tetrabutylammonium fluoride, partially still present triethylsilyl groups are cleaved. After mixing with water, extraction with ethyl acetate and concentration by evaporation, the crude product is chromatographed according to Example 1 on silica gel 60 (0.040–0.063 mm). The following products are isolated:
a) 3,17β-Dihydroxy-19-nor-17α-pregna-1,3,5(10)-triene-21,16α-lactone
    156 mg (19% of theory; $^1$H-NMR data and melting points, see Table 1)
b) 17β-Cyanomethyl-estra-1,3,5(10)-triene-3,16α,17α-triol
    270 mg (33% of theory; $^1$H-NMR data, see Example 1)
c) 17α-Cyanomethyl-estra-1,3,5(10)-triene-3,16α,17β-triol
    343 mg (42% of theory) $^1$H-NMR data (400 MHz, DMSO-d$_6$, TMS): 8.98 (s, 3-OH); 7.02 (d, J=8.6 Hz, H-1); 6.49 (dd, J=8.6/2.5 Hz, H-2); 6.41 (d, J=2.5 Hz, H-4); 5.07 (s, 17-OH); 4.98 (d, J=5.1 Hz, 16-OH); 4.11 (m, H-16); 2.68 (m, H-6); 2.76 and 2.54 (—CH$_2$CN, AB-system JAB=16.6 Hz); 0.81 (s, H-18)

EXAMPLE 3

The reaction of 1.28 g (2.5 mmol) of 3,16α-bis (tert-butyldimethylsilyloxy)-estra-1,3,5(10)-trien-17-one is carried out according to Example 1. The crude product that is obtained is dissolved in tetrahydrofuran, whereby by adding tetrabutylammonium fluoride, still present tert-butyldimethylsilyl groups are cleaved. After mixing with water, extraction with ethyl acetate and concentration by evaporation, the crude product is chromatographed according to Example 1 on silica gel 60 (0.040–0.063 mm).

The following products are isolated:
a) 3,17β-Dihydroxy-19-nor-17α-pregna-1,3,5(10)-triene-21,16α-lactone
    49 mg (6% of theory) ($^1$H-NMR data and melting points, see Table 1)
b) 17α-Cyanomethyl-estra-1,3,5(10)-triene-3,16α,17α-triol
    311 mg (38% of theory) ($^1$H-NMR data, see Example 1)
c) 17α-Cyanomethyl-estra-1,3,5(10)-triene-3,16α,17β-triol
    392 mg (48% of theory) ($^1$H-NMR data, see Example 2)

EXAMPLE 4

961 mg (2.5 mmol) of 17-oxo-18a-homo-estra-1,3,5(10)-triene-3,16α-diyldiacetate is reacted according to Example 1, and the crude product that is obtained is separated chromatographically.

The following products are isolated:
a) 3,17β-Dihydroxy-18a-homo-19-nor-17α-pregna-1,3,5(10)-triene-21,16α-lactone
    454 mg (53% of theory) ($^1$H-NMR data and melting points, see Table 1)
b) 17β-Cyanomethyl-18a-homo-estra-1,3,5(10)-triene-3,16α, 17α-triol
    188 mg (22% of theory)

EXAMPLE 5

1.00 g (2.5 mmol) of 11β-methoxy-17-oxo-estra-1,3,5(10)-triene-3,16α-diylacetate is reacted according to Example 1, and the crude product that is obtained is separated chromatographically.

The following products are isolated:
a) 3,17β-Dihydroxy-11β-methoxy-19-nor-17α-pregna-1,3,5(10)-triene-21,16α-lactone
    439 mg (49% of theory) ($^1$H-NMR data and melting points, see Table 1)
b) 17β-Cyanomethyl-11β-methoxy-estra-1,3,5(10)-triene-3,16α,17α-triol
    223 mg (25% of theory)

EXAMPLE 6

856 mg (2.5 mmol) of 3-methoxy-17-oxo-estra-1,3,5(10)-trien-16α-ylacetate is reacted according to Example 1, and the crude product that is obtained is separated chromatographically with the aid of the eluant cyclohexane/ethyl acetate (2/1).

The following products are isolated:
a) 17β-Hydroxy-3-methoxy-19-nor-17α-pregna-1,3,5(10)-triene-21,16α-lactone
    445 mg (52% of theory) ($^1$H-NMR data and melting points, see Table 1)
b) 17β-Cyanomethyl-3-methoxy-estra-1,3,5(10)-triene-16α,17α-diol
    265 mg (31% of theory)

EXAMPLE 7

891 mg (2.5 mmol) of 3-methoxy-17-oxo-18a-homo-estra-1,3,5(10)-trien-16α-ylacetate is reacted according to Example 1, and the crude product that is obtained is separated chromatographically with the aid of the eluant cyclohexane/ethyl acetate (2/1).

The following products are isolated:
a) 17β-Hydroxy-3-methoxy-18a-homo-19-nor-17α-pregna-1,3,5(10)-triene-21,16α-lactone
544 mg (61% of theory) ($^1$H-NMR data and melting points, see Table 1)
b) 17β-Cyanomethyl-3-methoxy-18a-homo-estra-1,3,5(10)-triene-16α,17α-diol
133 mg (15% of theory)

EXAMPLE 8

921 mg (2.5 mmol) of 17-oxo-estra-1,3,5(10),9(11)-triene-3,16α-diyldiacetate is reacted according to Example 1, and the crude product that is obtained is separated chromatographically.

The following products are isolated:
a) 3,17β-Dihydroxy-19-nor-17α-pregna-1,3,5(10),9(11)-tetraene-21,16α-lactone
375 mg (46% of theory) ($^1$H-NMR data and melting points, see Table 1)
b) 17β-Cyanomethyl-estra-1,3,5(10),9(11)-tetraene-3,16α,17α-triol
122 mg (15% of theory)

TABLE 1

19-Nor-17α-pregna-1,3,5(10)-trienes with a 21,16α- Lactone Ring

| Ex. | Compound | Yield (% of theory) | $^1$H NMR Data (400 MHz, DMSO-d$_6$, TMS) | Melting Point ° C. |
|---|---|---|---|---|
| 1 | 3,17β-Dihydroxy-19-nor-17α-pregna-1,3,5(10)-triene-21,16α-lactone | 58 | 9.00 (s, 3-OH; 7.03 (d, J = 8.5 Hz, H-1); 6.50 (dd, J = 8.5/2.5 Hz, H-2); 6.42 (d, J = 2.5 Hz, H-4); 5.47 (s, 17-OH); 4.65 (d, J = 7.8 Hz, H-16); 3.09 (d, J = 18.7 Hz, H-20); 2.69 (m, H-6); 2.27 (d, J = 18.7 Hz, H-20); 0.82 (s, H-18) | 319–324° C. (DSC) |
| 2 | 3,17β-Dihydroxy-19-nor-17α-pregna-1,3,5(10)-triene-21,16α-lactone | 19 | 9.00 (s, 3-OH; 7.03 (d, J = 8.5 Hz, H-1); 6.50 (dd, J = 8.5/2.5 Hz, H-2); 6.42 (d, J = 2.5 Hz, H-4); 5.47 (s, 17-OH); 4.65 (d, J = 7.8 Hz, H-16); 3.09 (d, J = 18.7 Hz, H-20); 2.69 (m, H-6); 2.27 (d, J = 18.7 Hz, H-20); 0.82 (s, H-18) | |
| 3 | 3,17β-Dihydroxy-19-nor-17α-pregna-1,3,5(10)-triene-21,16α-lactone | 6 | 9.00 (s, 3-OH; 7.03 (d, J = 8.5 Hz, H-1); 6.50 (dd, J = 8.5/2.5 Hz, H-2); 6.42 (d, J = 2.5 Hz, H-4); 5.47 (s, 17-OH); 4.65 (d, J = 7.8 Hz, H-16); 3.09 (d, J = 18.7 Hz, H-20); 2.69 (m, H-6); 2.27 (d, J = 18.7 Hz, H-20); 0.82 (s, H-18) | |
| 4 | 3,17β-Dihydroxy-18a-homo-19-nor-17α-pregna-1,3,5(10)-triene-21,16α-lactone | 53 | 9.02 (s, 3-OH); 7.02 (d, J = 8.6 Hz, H-1); 6.50 (dd, J = 8.6/2.5 Hz, H-2); 6.43 (d, J = 2.5 Hz, H-4); 5.47 (s, 17-OH); 4.71 (d, J = 7.4 Hz, H-16); 3.10 (d, J = 18.7 Hz, H-20); 2.69 (m, H-6); 2.27 (d, J = 18.7 Hz, H-20); 0.94 (t, J = 6.6 Hz, H-18a) | 265–270° C. |
| 5 | 3,17β-Dihydroxy-11β-methoxy-19-nor-17α-pregna-1,3,5(10)-triene-21,16α-lactone | 49 | 8.96 (s, 3-OH); 6.93 (d, J = 8.5 Hz, H-1); 6.50 (dd, J = 8.6/2.3 Hz, H-2); 6.40 (d, J = 2.3 Hz, H-4); 5.48 (s, 17-OH); 4.64 (d, J = 7.8 Hz, H-16); 3.14 (s, 11-OCH$_3$); 3.10 (d, J = 18.7 Hz, H-20); 2.64 (m, H-6); 2.26 (d, J = 18.7 Hz, H-20), 0.98 (s, H-18) | 251–264° C. |
| 6 | 17β-Hydroxy-3-methoxy-19-nor-17α-pregna-1,3,5(10)-triene-21, 16α-lactone | 52 | 7.15 (d., J = 8.3 Hz, H-1); 6.66 (dd, J = 8.3/2.3 Hz, H-2); 6.60 (d, J = 2.3 Hz, H-4); 5.48 (s, 17-OH) 4.65 (d, J = 7.4 Hz, H-16); 3.68 (s, 3-OCH$_3$); 3.09 (d, J = 18.7 Hz H-20); 2.76 (m, H-6); 2.27 (d, J = 18.7 Hz, H-20); 0.82 (s, H-18) | 177–180° C. |
| 7 | 17β-Hydroxy-3-methoxy-18a-homo-19-nor-17α-pregna-1,3,5(10)-triene-21,16α-lactone | 61 | 7.14 (d, J = 8.6 Hz, H-1); 6.66 (dd, J = 8.6/2.5 Hz, H-2); 6.60 (d, J = 2.5 Hz, H-4); 5.44 (s, 17-OH); 4.71 (d, J = 7.4 Hz, H-16); 3.68 (s, 3-OCH$_3$); 3.11 (d, J = 18.5 Hz, H-20); 2.78 (m, H-6); 2.26 (d, J = 18.5 Hz, H-20); 0.94 (t, J = 7.0 Hz, H-18a) | 240–248° C. |
| 8 | 3,17β Dihydroxy-19-nor-17α-pregna-1,3,5(10),9(11)-tetraene-21,16α-lactone | 46 | 9.25 (s, 3-OH); 7.41 (d, J = 8.5 Hz, H-1); 6.53 (dd, J = 8.5/2.3 Hz, H-2); 6.43 (d, J = 2.3 Hz, H-4); 6.05 (t, J = 2.5 Hz, H-11) 5.53 (s, 17-OH); 4.69 (d, J = 7.4 Hz, H-16); 3.01 (d, J = 18.4 Hz, H-20); 2.69 (m, H-6); 2.27 (d, J = 18.4 Hz, H-20); 0.81 (s, H-18) | 289–295° C. |

The preceding examples can be repeated with similar success by substituting the generically or specifically described reactants and/or operating conditions of this invention for those used&in the preceding examples.

From the foregoing description, one skilled in the art can easily ascertain the essential characteristics of this invention and, without departing from the spirit and scope thereof, can make various changes and modifications of the invention to adapt it to various usages and conditions.

What is claimed is:

1. A 19-Nor-17α-pregna-1,3,5(10)-triene with a 21, 16 α-lactone ring of formula (II)

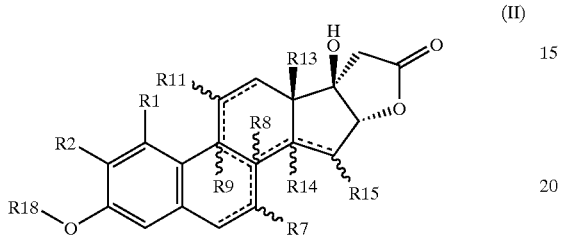

(II)

in which the dotted lines in rings B, C and D optionally mean one or two double bonds, $R^1$ is a halogen atom, a hydroxyl, methyl, trifluoromethyl, methoxy or ethoxy group or a hydrogen atom, $R^2$ is a halogen atom, a hydroxyl group, a straight-chain or branched-chain, saturated or unsaturated alkoxy group with 1 to 6 carbon atoms or a hydrogen atom, is an α- or β-position halogen atom, an α- or β-position, straight-chain or branched-chain, saturated or unsaturated, optionally partially or completely fluorinated alkyl group with up to 10 carbon atoms, a straight-chain or branched-chain, saturated or unsaturated alkoxy group with up to 6 carbon atoms, an optionally substituted aryl or heteroaryl radical or a hydrogen atom, $R^8$ is an α- or β-position hydrogen atom, an α- or β-position, straight-chain or branched-chain, saturated or unsaturated, optionally partially or completely fluorinated alkyl group with up to 10 carbon atoms or an α- or β-position cyano group, $R^9$ is an α- or β-position hydrogen atom, an α- or β-position methyl, ethyl, trifluoromethyl or pentafluoroethyl group, is an α- or β-position nitrooxy group, an α- or β-position hydroxyl- or mercapto group, an α- or β-position halogen atom, an α- or β-position chloromethyl group, an α- or β-position, straight-chain or branched-chain, saturated or unsaturated, optionally partially or completely fluorinated alkyl group with up to 17 carbon atoms, an α- or β-position, straight-chain or branched-chain, saturated or unsaturated alkoxy or alkylthio group with up to 6 carbon atoms, an optionally substituted, α- or β-position aryl or heteroaryl radical or hydrogen atom, $R^{13}$ is a methyl or ethyl group, $R^{14}$ is an α- or β-position, straight-chain or branched-chain, saturated or unsaturated, optionally partially or completely fluorinated alkyl group with up to 10 carbon atoms or an α- or β-position hydrogen atom, $R^{15}$ is an α- or β-position, straight-chain or branched-chain, saturated or unsaturated, optionally partially or completely fluorinated alkyl group with up to 10 carbon atoms or an α- or β-position hydrogen atom, or $R^{14}$ and $R^{15}$ together are a 14β,15β-methylene group that is optionally substituted with one or two halogen atoms, and $R^{18}$ is a hydrogen atom, a methyl, $C_{2-6}$acyl or tri($C_{1-4}$alkyl)silyl group or a group $R^{19}SO_2$, wherein $R^{19}$ is a group $R^{20}R^{21}N$, wherein $R^{20}$ and $R^{21}$, independently of one another, are a hydrogen atom, a $C_{1-5}$alkyl radical, a group $C(O)R^{22}$, in which $R^{22}$ optionally contains a straight-chain or branched hydrocarbon radical with up to 12 carbon atoms, which in addition optionally contains up to three double bonds, a $C_{3-7}$cycloalkyl radical, an aryl radical or a combination of these structural features, or together with the N-atom are a polymethylenimino radical with 4 to 6 C atoms or a morpholino radical, wherein the 3,17β-dihydroxy-2-methoxyl-19-nor-17α-pregna-1,3,5(10)-triene-21,16α-lactone is excluded.

2. A 19-Nor-17α-pregna-1,3,5(10)-triene with a 21,16α-lactone ring according to claim 1 of formula (IIa)

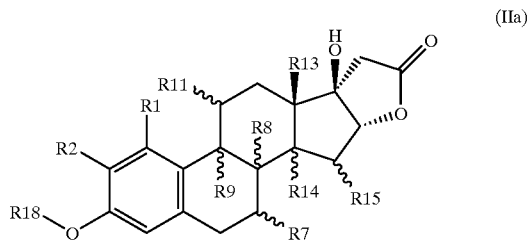

(IIa)

in which $R^1$, $R^2$, $R^7$ to $R^9$, $R^{11}$, $R^{13}$ to $R^{15}$ and $R^{18}$ are defined as in claim 1.

3. A 19-Nor-17α-pregna-1,3,5(10)-triene with a 21,16α-lactone ring according to claim 2, wherein $R^1$, $R^2$, $R^7$, $R^8$, $R^{11}$ and $R^{13}$ to $R^{15}$ are each a hydrogen atom, $R^9$ is a $C_{1-4}$alkyl group, and $R^{18}$ is a hydrogen atom or a methyl group.

4. A 19-Nor-17α-pregna-1,3,5(10)-triene with a 21,16α-lactone ring according to claim 2, wherein $R^1$, $R^2$, $R^7$, $R^8$, $R^9$ and $R^{13}$ to $R^{15}$ are each a hydrogen atom, $R^{11}$ is a $C_{1-6}$alkyl group, $C_{1-6}$alkoxy group, vinyl group or phenyl group, and $R^{18}$ is a hydrogen atom or a methyl group.

5. A 19-Nor-17α-pregna-1,3,5(10)-triene with a 21,16α-lactone ring according to claim 2, wherein $R^1$, $R^2$, $R^8$, $R^9$, $R^{11}$ and $R^{13}$ to $R^{15}$ are each a hydrogen atom, $R^7$ is a $C_{1-4}$alkyl group, $C_{1-4}$alkoxy group, vinyl group or phenyl group, and $R^{18}$ is a hydrogen atom or a methyl group.

6. A 19-Nor-17α-pregna-1,3,5(10)-triene with a 21,16α-lactone ring according to claim 1 of formula (IIb),

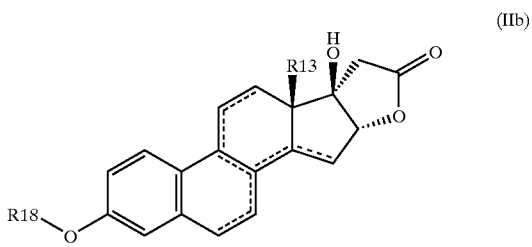

(IIb)

in which the dotted lines in rings B, C and D optionally mean one or two double bonds, and $R^{13}$ and $R^{18}$ are as defined in claim 1.

7. A 19-Nor-17α-pregna-1,3,5(10)-triene with a 21,16α-lactone ring according to claim 6, having, independently of one another, an additional double bond in the 7,8-position, 6,7-position, 8,9-position, or 9,11-position.

23

8. A 19-Nor-17α-pregna-1,3,5(10)-triene with a 21,16α-lactone ring according to claim 7, wherein $R^{18}$ is a hydrogen atom or a methyl group.

9. A 19-Nor-17α-pregna-1,3,5(10)-triene with a 21,16α-lactone ring according to claim 2, which is 3,17β-Dihydroxy-11β-methyl-19-nor-17α-pregna-1,3,5(10)-triene-21,16α-lactone, 3,17β-Dihydroxy-3-methoxy-11β-methyl-19-nor-17α-pregna-1,3,5(10)-triene-21,16α-lactone, 3,17β-Dihydroxy-11β-methoxy-19-nor-17α-pregna-1,3,5(10)-triene-21,16α-lactone, 3,17α-Dihydroxy-3,11β-dimethoxy-19-nor-17α-pregna-1,3,5(10)-triene-21,16α-lactone, 3,17β-Dihydroxy-11β-ethyl-19-nor-17α-pregna-1,3,5(10)-triene-21,16α-lactone, 3,17β-Dihydroxy-11β-ethyl-3-methoxy-19-nor-17α-pregna-1,3,5(10)-triene-21,16α-lactone, 3,17β-Dihydroxy-11β-phenyl-19-nor-17α-pregna-1,3,5(10)-triene-21,16α-lactone, 3,17β-Dihydroxy-3-methoxy-11β-phenyl-19-nor-17α-pregna-1,3,5(10)-triene-21,16α-lactone, 3,17β-Dihydroxy-11β-vinyl-19-nor-17α-pregna-1,3,5(10)-triene-21,16α-lactone, 3,17β-Dihydroxy-3-methoxy-11β-vinyl-19-nor-17α-pregna-1,3,5(10)-triene-21,16α-lactone, 3,17β-Dihydroxy-7β-methyl-19-nor-17α-pregna-1,3,5(10)-triene-21,16α-lactone, 3,17β-Dihydroxy-3-methoxy-7β-methyl-19-nor-17α-pregna-1,3,5(10)-triene-21,16α-lactone, 3,17β-Dihydroxy-7β-methoxy-19-nor-17α-pregna-1,3,5(10)-triene-21,16α-lactone, 3,17β-Dihydroxy-3,7β-dimethoxy-19-nor-17α-pregna-1,3,5(10)-triene-21,16α-lactone, 3,17β-Dihydroxy-7β-ethyl-19-nor-17α-pregna-1,3,5(10)-triene-21,16α-lactone, 3,17β-Dihydroxy-7β-ethyl-3-methoxy-19-nor-17α-pregna-1,3,5(10)-triene-21,16α-lactone, 3,17β-Dihydroxy-7β-phenyl-19-nor-17α-pregna-1,3,5(10)-triene-21,16α-lactone, 3,17β-Dihydroxy-3-methoxy-7β-phenyl-19-nor-17α-pregna-1,3,5(10)-triene-21,16α-lactone, 3,17β-Dihydroxy-7β-vinyl-19-nor17α-pregna-1,3,5(10)-triene-21,16α-lactone, 3,17β-Dihydroxy-3-methoxy-7β-vinyl-19-nor-17α-pregna-1,3,5(10)-triene-21,16α-lactone, 3,17β-Dihydroxy-7α-methyl-19-nor-17α-pregna-1,3,5(10)-triene-21,16α-lactone, 3,17β-Dihydroxy-3-methoxy-7α-methyl-19-nor-17α-pregna-1,3,5(10)-triene-21,16α-lactone, 3,17β-Dihydroxy-7α-methoxy-19-nor-17α-pregna-1,3,5(10)-triene-21,16α-lactone, 3,17β-Dihydroxy-3,7α-dimethoxy-19-nor-17α-pregna-1,3,5(10)-triene-21,16α-lactone, 3,17β-Dihydroxy-7α-ethyl-19-nor-17α-pregna-1,3,5(10)-triene-21,16α-lactone, 3,17β-Dihydroxy-7α-ethyl-3-methoxy-19-nor17α-pregna-1,3,5(10)-triene-21,16α-lactone, 3,17β-Dihydroxy-7α-phenyl-19-nor-17α-pregna-1,3,5(10)-triene-21,16α-lactone, 3,17β-Dihydroxy-3-methoxy-7α-Phenyl-19-nor17α-pregna-1,3,5(10)-triene-21,16α-lactone, 3,17β-Dihydroxy-7α-vinyl-19-nor-17α-pregna-1,3,5(10)-triene-21,16α-lactone, 3,17β-Dihydroxy-3-methoxy-7α-vinyl-19-nor-17α-pregna-1,3,5(10)-triene-21,16α-lactone, 3,17β-Dihydroxy-19-nor-17α-pregna-1,3,5(10)-triene-21,16α-lactone or 3,17β-Dihydroxy-3-methoxy-19-nor-17α-pregna-1,3,5(10)-triene-21,16α-lactone.

10. A 19-Nor-17α-pregna-1,3,5(10)-triene with a 21,16α-lactone ring according to claim 6, which is 3,17β-Dihydroxy-19-nor-17α-pregna-1,3,5(10),7-tetraene-21,16α-lactone, 3,17β-Dihydroxy-3-methoxy-19-nor-17α-pregna-1,3,5(10),7-tetraene-21,16α-lactone, 3,17β-Dihydroxy-19-nor-17α-pregna-1,3,5(10)6,8(9)-pentaene-21,16α-lactone, 3,17β-Dihydroxy-3-methoxy-19-nor-17α-pregna-1,3,5(10),6,8(9)-pentaene-21,16α-lactone, 3,17β-Dihydroxy-19-nor-17α-pregna-1,3,5(10),9-tetraene-21,16α-lactone, 3,17β-Dihydroxy-3-methoxyl-9-nor-17α-pregna-1,3,5(10),19-tetraene-21,16α-lactone, 3,17β-Dihydroxy-19-nor-17α-pregna-1,3,5(10),8(9)-tetraene-21,16α-lactone or 3,17β-Dihydroxy-3-methoxy-19-nor-17α-pregna-1,3,5(10),8(9)-tetraene-21,16α-lactone.

11. A 17α-Cyanomethylated estra-1,3,5(10)-triene of formula (I)

(I)

in which the dotted lines in rings B, C, and D optionally mean one or two double bonds, $R^1$ is a halogen atom, a hydroxyl, methyl, trifluoromethyl, methoxy or ethoxy group or a hydrogen atom, $R^2$ is a halogen atom, a hydroxyl group, a straight-chain or branched-chain, saturated or unsaturated alkoxy group with 2 to 6 carbon atoms or a hydrogen atom, $R^7$ is an α- or β-position halogen atom, an α- or β-position, straight-chain or branched-chain, saturated or unsaturated, optionally partially or completely fluorinated alkyl group with up to 10 carbon atoms, a straight-chain or branched-chain, saturated or unsaturated alkoxy group with up to 6 carbon atoms, an optionally substituted aryl or heteroaryl radical or a hydrogen atom, $R^8$ is an α- or β-position hydrogen atom, an α- or β-position, straight-chain or branched-chain, saturated or unsaturated, optionally partially or completely fluorinated alkyl group with up to 10 carbon atoms or an α- or β-position cyano group, $R^9$ is an α- or β-position hydrogen atom, an α- or β-position methyl, ethyl, trifluoromethyl or pentafluoroethyl group, $R^{11}$ is an α- or β-position nitrooxy group, an α- or β-position hydroxyl or mercapto group, an α- or β-position halogen atom, an α- or β-position chloromethyl group, an α- or β-position, straight-chain or branched-chain, saturated or unsaturated, optionally partially or completely fluorinated alkyl group with up to 10 carbon atoms, an α- or β-position, straight-chain or branched-chain, saturated or unsaturated alkoxy or alkylthio group with up to 6 carbon atoms, an optionally substituted, α- or β-position aryl or heteroaryl radical or hydrogen atom, $R^{13}$ is a methyl or ethyl group, $R^{14}$ is an α- or β-position, straight-chain or branched-chain, saturated or unsaturated, optionally partially or completely fluorinated alkyl group with up to 10 carbon atoms or an α- or β-position hydrogen atom, $R^{15}$ is an α- or β-position, straight-chain or branched-chain, saturated or unsaturated, optionally partially or completely fluorinated alkyl group with up to 10 carbon atoms or an α- or β-position hydrogen atom, or $R^{14}$ and $R^{15}$ together are a 14 α,15α-methylene or 14β, 15β-methylene group optionally substituted with one or two halogen atoms, $R^{18}$ is a hydrogen atom; a methyl-, acyl or silyl group or a group $R^{19}SO_2^-$, wherein $R^{19}$ is a group $R^{20}R^{21}N-$, wherein $R^{20}$ and $R^{21}$, independently of one another, are a hydrogen atom, a $C_{1-5}$alkyl radical, a group $C(O)R^{22}$, in which $R^{22}$ optionally contains a straight-chain or branched hydrocarbon radical with up to 12 carbon atoms, which in addition optionally contains up to three double bonds, a $C_{3-7}$cycloalkyl radical, an aryl radical or a combination of these structural features, or together with the N-atom are a polymethylenimino radical with 4 to 6 C atoms or a morpholino radical, and $R^{23}$ is a hydrogen atom, an acyl or silyl group, with the proviso that 17α-cyanomethylestra-1,3,5(10)-triene-3, 16-17-triol is excluded.

12. A 17α-Cyanomethylated estra-1,3,5(10)-triene according to claim 11 of formula (Ia)

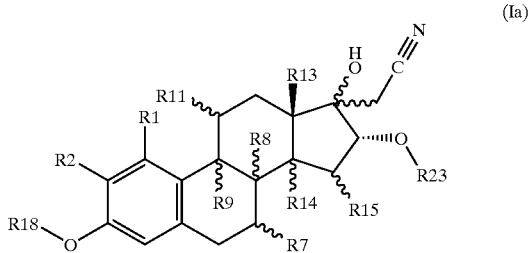

(Ia)

in which $R^1$, $R^2$, $R^7$ to $R^9$, $R^{11}$, $R^{13}$ to $R^{15}$, $R^{18}$ and $R^{23}$ are defined as in claim 11.

13. A 17α-Cyanomethylated estra-1,3,5(10)-triene of formula (Ia)

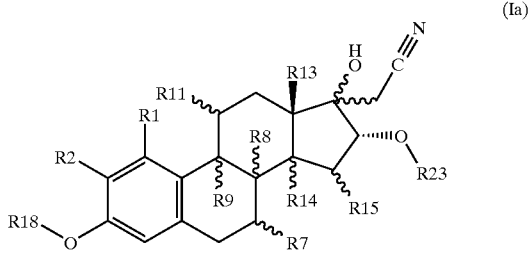

(Ia)

wherein $R^1$, $R^2$, $R^7$, $R^8$, $R^{11}$, $R^{13}$ to $R^{15}$ and $R^{23}$ are each a hydrogen atom, $R^9$ is a $C_{1-4}$alkyl group and $R^{18}$ is a hydrogen atom or a methyl group.

14. A 17α-Cyanomethylated estra-1,3,5(10)-triene according to claim 12, wherein $R^1$, $R^2$, $R^7$, $R^8$, $R^9$, $R^{13}$ to $R^{15}$ and $R^{23}$ are each a hydrogen atom, $R^{11}$ is a $C_{1-4}$alkyl group, $C_{1-4}$alkoxy group, vinyl group or phenyl group, and $R^{18}$ is a hydrogen atom or a methyl group.

15. A 17α-Cyanomethylated estra-1,3,5(10)-triene according to claim 12, wherein $R^1$, $R^2$, $R^8$, $R^9$, $R^{11}$, $R^{13}$ to $R^{15}$ and $R^{23}$ are each a hydrogen atom, $R^7$ is a $C_{1-4}$alkyl group, $C_{1-4}$alkoxy group, vinyl group or phenyl group, and $R^{18}$ is a hydrogen atom or a methyl group.

16. A 17α-Cyanomethylated estra-1,3,5(10)-triene according to claim 11 of formula (Ib)

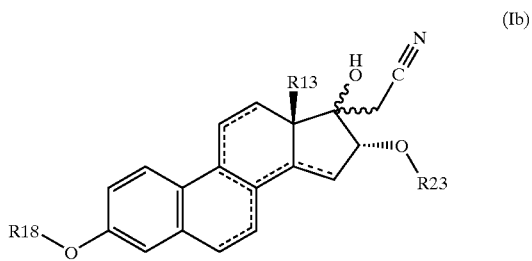

(Ib)

in which the dotted lines in rings B, C and D optionally mean one or two double bonds, and $R^{13}$, $R^{18}$ and $R^{23}$ are a s defined in claim 11.

17. A 17α-Cyanomethylated estra-1,3,5(10)-triene according to claim 16, having, independently of one another, an additional double bond in the 7,8-position, 6,7-position, 8,9-position, or 9,11-position.

18. A 17α-Cyanomethylated estra-1,3,5(10)-triene according to claim 17, wherein $R^{18}$ is a hydrogen atom or a methyl group.

19. A 17α-Cyanomethylated estra-1,3,5(10)-triene of according to claim 12, which is 17α-Cyanomethyl-9α-methyl-estra-1,3,5(10)-triene-3, 16α,17β-triol, 17α-Cyanomethyl-3-methoxy-9α-methyl-estra-1,3,5 (10)-triene-16α,17β-diol, 17α-Cyanomethyl-3-methoxy-estra-1,3,5(10)-triene-16α,17β-diol, 17α-Cyanomethyl-11β-methyl-estra-1,3,5(10)-triene-3, 16α,17β-triol, 17α-Cyanomethyl-11β-methyloxy-estra-1,3,5(10)-triene-3,16α,17β-triol, 17α-Cyanomethyl-11β-ethyl-estra-1,3,5(10)-triene-3, 16α,17β-triol, 17α-Cyanomethyl-11β-phenyl-estra-1,3,5(10)-triene-3, 16α,17β-triol, 17α-Cyanomethyl-11β-vinyl-estra-1,3,5(10)-triene-3, 16α,17β-triol, 17β-Cyanomethyl-11β-ethyl-estra-1,3,5(10)-triene-3, 16α,17α-triol, 17α-Cyanomethyl-7α-methyl-estra-1,3,5(10)-triene-3, 16α,17β-triol, 17α-Cyanomethyl-7α-ethyl-estra-1,3,5(10)-triene-3,16α, 17β-triol, 17α-Cyanomethyl-7α-Phenyl-estra-1,3,5(10)-triene-3, 16α,17β-triol, 17α-Cyanomethyl-7α-vinyl-estra-1,3,5(10)-triene-3,16α, 17β-triol, 17α-Cyanomethyl-3-methoxy-11β-methyl-estra-1,3,5 (10)-triene-16α,17β-diol, 17α-Cyanomethyl-3,11β-dimethoxy-estra-1,3,5(10)-triene-16α,17β-diol, 17α-Cyanomethyl-11β-ethyl-3-methoxy-estra-1,3,5(10)-triene-16α,17β-diol, 17α-Cyanomethyl-3-methoxy-11β-phenyl-estra-1,3,5(10)-triene-16α,17β-diol, 17α-Cyanomethyl-3-methoxy-11β-vinyl-estra-1,3,5(10)-triene-16α,17β-diol, 17α-Cyanomethyl-3-methoxy-6α-methyl-estra-1,3,5(10)-triene-16α,17β-diol, 17α-Cyanomethyl-7α-ethyl-3-methoxy-estra-1,3,5(10)-triene-16α,17β-diol, 17α-Cyanomethyl-3-methoxy-7α-Phenyl-estra-1,3,5(10)-triene-16α,17β-diol or 17α-Cyanomethyl-3-methoxy-7α-vinyl-estra-1,3,5(10)-triene-16α,17β-diol.

20. A 17α- Cyanomethylated estra-1,3,5(10)-triene of according to claim 16, which is 17α-Cyanomethyl-estra-1,3,5(10),7-tetraene-3,16α,17β-triol, 17α-Cyanomethyl-3-methoxy-estra-1,3,5(10),7-tetraene-16α,17β-triol, 17α-Cyanomethyl-estra-1,3,5(10),6,8(9)-pentaene-3,16α,17β-triol, 17α-Cyanomethyl-3-methoxy-estra-1,3,5(10),6,8(9)-pentaene-16α,17β-diol, 17α-Cyanomethyl-estra-1,3,5(10),9-tetraene-3,16α,17β-triol, 17α-Cyanomethyl-3-methoxy-estra-1,3,5(10),9-tetraene-16α,17β-diol, 17α-Cyanomethyl-estra-1,3,5(10),8(9)-tetraene-3,16α,17β-triol or 17α-Cyanomethyl-3-methoxy-estra-1,3,5(10),8(9)-tetraene-16α,17β-diol.

21. A process for preparing a 19-nor-17α-pregna-1,3,5(10)-triene with a 21,16α-lactone ring of formula (II) according to claim 1, comprising reacting lithium acetonitrile with a compound of formula (III),

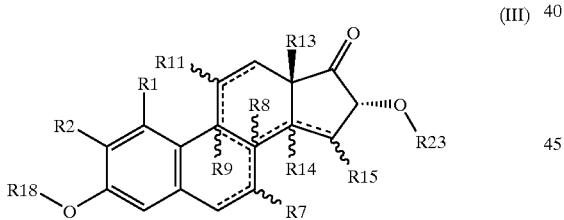

(III)

in which the dotted lines in rings B, C and D optionally mean one or two double bonds, $R^1$, $R^2$, $R^7$ to $R^9$, $R^{11}$, $R^{13}$ to $R^{15}$ and $R^{18}$ are defined as in claim 1, and $R^{23}$ is an acetyl or trimethylsilyl group.

22. A pharmaceutical composition comprising at least one 19-nor-17α-pregna-1,3,5(10)-triene with a 21,16α-lactone ring according to claim 1 and a pharmaceutically acceptable adjuvant or vehicle.

23. A 19-Nor-17α-pregna-1,3,5(10)-triene with a 21,16α-lactone ring according to claim 6, having, independently of one another, an additional double bond in the 6,7-position or 8,9-position.

24. A 17α-Cyanomethylated estra-1,3,5(10)-triene according to claim 16, having, independently of one another, an additional double bond in the 6,7-position or 8,9-position.

25. A method for hormone therapy comprising administering a pharmaceutical composition according to claim 22 to a patient in need thereof.

26. A method for treating rheumatoid arthritis comprising administering a pharmaceutical composition according to claim 22 to a patient in need thereof.

27. A method for treating hot flashes, sleep disturbances, irritability, mood swings, incontinence, or vaginal atrophy comprising administering a pharmaceutical composition according to claim 22 to a patient in need thereof.

28. A method for preventing conception comprising administering a pharmaceutical composition according to claim 22 to a patient in need thereof.

29. A method for prophylaxis of hormone-deficiency-induced bone mass loss or osteoporosis comprising administering a pharmaceutical composition according to claim 23 to a patient in need thereof.

30. A method for promoting wound healing comprising administering a pharmaceutical composition according to claim 22 to a patient in need thereof.

31. A method for therapy of prostate cancer comprising administering a pharmaceutical composition according to claim 22 to a patient in need thereof.

32. A process for preparing a 17α- and 17β-cyanomethylated estra-1,3,5(10)-triene of formula (I')

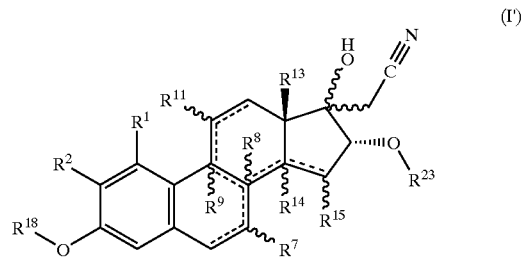

(I')

in which the dotted lines in rings B, C, and D optionally mean one or two double bonds, $R^1$ is a halogen atom, a hydroxyl, methyl, trifluoromethyl, methoxy or ethoxy group or a hydrogen atom, $R^2$ is a halogen atom, a hydroxyl group, a straight-chain or branched-chain, saturated or unsaturated alkoxy group with 2 to 6 carbon atoms or a hydrogen atom, $R^7$ is an α- or β-position halogen atom, an α- or β-position, straight-chain or branched-chain, saturated or unsaturated, optionally partially or completely fluorinated alkyl group with up to 10 carbon atoms, a straight-chain or branched-chain, saturated or unsaturated alkoxy group with up to 6 carbon atoms, an optionally substituted aryl or heteroaryl radical or a hydrogen atom, $R^8$ is an α- or β-position hydrogen atom, an α- or β-position, straight-chain or branched-chain, saturated or unsaturated, optionally partially or completely fluorinated alkyl group with up to 10 carbon atoms or an α- or β-position cyano group, $R^9$ is an α- or β-position hydrogen atom, an α- or β-position methyl, ethyl, trifluoromethyl or pentafluoroethyl group, $R^{11}$ is an α- or β-position nitrooxy group, an α- or β-position hydroxyl or mercapto group, an α- or β-position halogen atom, an α- or β-position chloromethyl group, an α- or β-position, straight-chain or branched-chain, saturated or unsaturated, optionally partially or completely fluorinated alkyl group with up to 10 carbon atoms, an α- or β-position, straight-chain or branched-chain, saturated or unsaturated alkoxy or alkylthio group with up to 6 carbon atoms, an optionally substituted, α- or β-position aryl or heteroaryl radical or hydrogen atom, $R^{13}$ is a methyl or ethyl group, $R^{14}$ is an α- or β-position, straight-chain or branched-chain, saturated or unsaturated, optionally partially or completely fluorinated alkyl group with up to 10 carbon atoms or an α- or β-position hydrogen atom, $R^{15}$ is an α- or β-position, straight-chain or branched-chain, saturated or unsaturated, optionally partially or completely fluorinated alkyl group with up to 10 carbon atoms or an α- or β-position hydrogen atom, or $R^{14}$ and $R^{15}$ together are a 14α15α-methylene or 14β,15β-methylene group optionally substituted with one or two halogen atoms, $R^{18}$ is a hydrogen atom; a methyl-, $C_{2-6}$ acyl or tri($C_{1-4}$alkyl)silyl group or a group $R^{19}SO_2^-$, wherein $R^{19}$ is a group $R^{20}R^{21}N-$, where in $R^{20}$ and $R^{21}$, independently of one another, are each a hydrogen atom, a $C_{1-5}$alkyl radical, a group $C(O)R^{22}$, in which $R^{22}$ optionally contains a straight-chain or branched hydrocarbon radical with up to 12 carbon atoms, which in addition optionally contains up to three double bonds, a $C_{3-7}$cycloalkyl radical, an aryl radical or a combination of these structural features, or together with the N-atom are a polymethylenimino radical with 4 to 6 C atoms or a morpholino radical, and $R^{23}$ is a hydrogen atom, a $C_{2-6}$acyl or tri($C_{1-4}$alkyl)silyl group, comprising reacting lithium acetonitrile with a compound of formula (III),

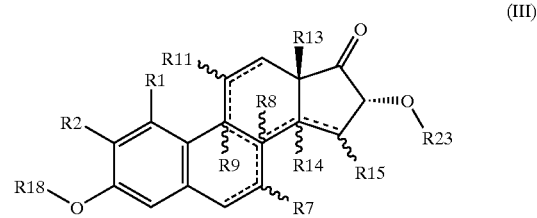

(III)

in which the dotted lines in rings B, C and D optionally mean one or two double bonds, $R^1$, $R^2$, $R^7$ to $R^9$, $R^{11}$, $R^{13}$ to $R^{15}$ and $R^{18}$ are defined as in claim 1, and $R^{23}$ is an acetyl or trimethylsilyl group.

\* \* \* \* \*

UNITED STATES PATENT AND TRADEMARK OFFICE
CERTIFICATE OF CORRECTION

PATENT NO.     : 6,670,347 B2
DATED          : December 30, 2003
INVENTOR(S)    : Müller et al.

It is certified that error appears in the above-identified patent and that said Letters Patent is hereby corrected as shown below:

Column 21,
Line 31, insert -- $R^7$ -- before "is".
Line 47, insert -- $R^{11}$ -- before "is".

Column 22,
Line 15, "methoxyl" should be -- methoxy --.

Column 23,
Line 45, "nor17α" should be -- nor-17α --.
Line 59, "nor17α" should be -- nor-17α --.
Line 63, "nor17α" should be -- nor-17α --.

Column 24,
Line 21, "methoxyl" should be -- methoxy --.

Column 26,
Line 27, "a s" should be -- as --.
Line 46, "methyloxy" should be -- methoxy --.
Line 61, "Phenyl" should be -- phenyl --.

Column 27,
Line 13, "Phenyl" should be -- phenyl --.

Column 28,
Line 13, "claim 23" should be -- claim 22 --.

UNITED STATES PATENT AND TRADEMARK OFFICE
CERTIFICATE OF CORRECTION

PATENT NO. : 6,670,347 B2
DATED : December 30, 2003
INVENTOR(S) : Müller et al.

It is certified that error appears in the above-identified patent and that said Letters Patent is hereby corrected as shown below:

Column 29,
Line 13, "14α15α" should be -- 14α, 15α --.
Line 18, "where in" should be -- wherein --.

Signed and Sealed this

Twenty-second Day of March, 2005

JON W. DUDAS
*Director of the United States Patent and Trademark Office*

UNITED STATES PATENT AND TRADEMARK OFFICE
CERTIFICATE OF CORRECTION

PATENT NO. : 6,670,347 B2
APPLICATION NO. : 09/963685
DATED : December 30, 2003
INVENTOR(S) : Müller et al.

It is certified that error appears in the above-identified patent and that said Letters Patent is hereby corrected as shown below:

Column 22
Line 34: "$R^{13}$" should be --$R^{14}$--.
Line 39: "$R^{13}$" should be --$R^{14}$--.
Line 44: "$R^{13}$" should be --$R^{14}$--.

Column 25
Line 65: "$R^{13}$" should be --$R^{14}$--.
Line 66: after "hydrogen atom," insert --$R^{13}$ is a methyl or ethyl group,--.

Column 26
Line 2: "$R^{13}$" should be --$R^{14}$--.
Line 7: "$R^{13}$" should be --$R^{14}$--.

Signed and Sealed this

Third Day of October, 2006

JON W. DUDAS
*Director of the United States Patent and Trademark Office*